(12) United States Patent
Li et al.

(10) Patent No.: US 11,359,007 B2
(45) Date of Patent: Jun. 14, 2022

(54) ANTI-SARS-COV-2 NEUTRALIZING ANTIBODIES

(71) Applicant: NEWSOARA BIOPHARMA CO., LTD., Shanghai (CN)

(72) Inventors: Yuannian Li, Shanghai (CN); Wenyi Wang, Shanghai (CN)

(73) Assignee: NEWSOARA BIOPHARMA CO., LTD., Shanghai (CN)

(*) Notice: Subject to any disclaimer, the term of this patent is extended or adjusted under 35 U.S.C. 154(b) by 0 days.

(21) Appl. No.: 17/391,161

(22) Filed: Aug. 2, 2021

(65) Prior Publication Data
US 2022/0073594 A1 Mar. 10, 2022

(30) Foreign Application Priority Data
Sep. 4, 2020 (WO) ............. PCT/CN2020/113404

(51) Int. Cl.
*C07K 16/10* (2006.01)
*A61K 45/06* (2006.01)

(52) U.S. Cl.
CPC .......... *C07K 16/10* (2013.01); *A61K 45/06* (2013.01); *C07K 2317/565* (2013.01); *C07K 2317/76* (2013.01)

(58) Field of Classification Search
None
See application file for complete search history.

(56) References Cited

FOREIGN PATENT DOCUMENTS

| CN | 111303280 A | 6/2020 |
|---|---|---|
| CN | 111423508 A | 7/2020 |
| CN | 111592594 A | 8/2020 |
| CN | 111592595 A | 8/2020 |
| CN | 111690058 A | 9/2020 |
| CN | 111825762 A | 10/2020 |
| CN | 111995674 A | 11/2020 |
| CN | 112010963 A | 12/2020 |
| CN | 112094340 A | 12/2020 |
| CN | 112175073 A | 1/2021 |
| CN | 112225797 A | 1/2021 |
| CN | 112225806 A | 1/2021 |
| CN | 112300274 A | 2/2021 |
| CN | 112442120 A | 3/2021 |
| CN | 112552399 A | 3/2021 |
| WO | 2005060520 A2 | 7/2005 |

OTHER PUBLICATIONS

Janeway et al., Immunobiology, 3rd edition, 1997, Garland Publishing Inc., pp. 3:1-3:21.*
Wang et al., "A human monoclonal antibody blocking SARS-CoV-2 infection," Nature Communications vol. 11, Article No. 2251, May 4, 2020.
The Australian Examination Report, dated Sep. 10, 2021, in the related Australian Appl. No. 2021209282.
Ju et al., "Potent human neutralizing antibodies elicited by SARS-CoV-2 infection," BioRxiv preprint, posted online Mar. 26, 2020.
Liu et al., "Potent Neutralizing Monoclonal Antibodies Directed to Multiple Epitopes on the SARS-CoV-2 Spike," BioRxiv preprint, posted online Jun. 18, 2020, URL: https://doi.org/10.1101/2020.06.17.153486.
Rogers et al., "Rapid isolation of potent SARS-CoV-2 neutralizing antibodies and protection in a small animal model," BioRxiv preprint, posted online May 15, 2020, URL: https://doi.org/10.1101/2020.05.11.088674.
Zhang et al., "Protein and Enzyme Engineering," Hefei University of Technology Press, 1st edition, Chapter 10, pp. 201-206, Sep. 2015. The English concise explanation of the relevance included.

* cited by examiner

*Primary Examiner* — Michael Szperka

(57) ABSTRACT

The present disclosure provides novel neutralizing antibodies against SARS-COV-2, and the antigen binding fragments thereof. Pharmaceutical composition and kits comprising the same, and the uses thereof are also provided.

1 Claim, 3 Drawing Sheets

Specification includes a Sequence Listing.

SEQUENCE LISTING

```
<160> NUMBER OF SEQ ID NOS: 30

<210> SEQ ID NO 1
<211> LENGTH: 5
<212> TYPE: PRT
<213> ORGANISM: Artificial Sequence
<220> FEATURE:
<223> OTHER INFORMATION: synthetic

<400> SEQUENCE: 1

Ser Tyr Asp Ile Asn
1               5

<210> SEQ ID NO 2
<211> LENGTH: 17
<212> TYPE: PRT
<213> ORGANISM: Artificial Sequence
<220> FEATURE:
<223> OTHER INFORMATION: Synthetic

<400> SEQUENCE: 2
```

```
Trp Met Asn Pro Asn Ser Ala Asn Pro Gly Tyr Ala Gln Lys Phe Gln
1               5                   10                  15

Gly

<210> SEQ ID NO 3
<211> LENGTH: 20
<212> TYPE: PRT
<213> ORGANISM: Artificial Sequence
<220> FEATURE:
<223> OTHER INFORMATION: Synthetic

<400> SEQUENCE: 3

Ala Arg Val Thr Ile His Tyr Asp Ile Leu Thr Gly Tyr Tyr Ser Asn
1               5                   10                  15

Ala Phe Asp Ile
            20

<210> SEQ ID NO 4
<211> LENGTH: 11
<212> TYPE: PRT
<213> ORGANISM: Artificial Sequence
<220> FEATURE:
<223> OTHER INFORMATION: Synthetic

<400> SEQUENCE: 4

Arg Ala Ser Gln Thr Ile Ser Ser Tyr Leu Asn
1               5                   10

<210> SEQ ID NO 5
<211> LENGTH: 7
<212> TYPE: PRT
<213> ORGANISM: Artificial Sequence
<220> FEATURE:
<223> OTHER INFORMATION: Synthetic

<400> SEQUENCE: 5

Ala Ala Ser Ser Leu Gln Ser
1               5

<210> SEQ ID NO 6
<211> LENGTH: 10
<212> TYPE: PRT
<213> ORGANISM: Artificial Sequence
<220> FEATURE:
<223> OTHER INFORMATION: Synthetic

<400> SEQUENCE: 6

Gln Gln Ser Tyr Thr Thr Phe Met Tyr Thr
1               5                   10

<210> SEQ ID NO 7
<211> LENGTH: 129
<212> TYPE: PRT
<213> ORGANISM: Artificial Sequence
<220> FEATURE:
<223> OTHER INFORMATION: Synthetic

<400> SEQUENCE: 7

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Asp Ile Asn Trp Val Arg Gln Ala Ser Gly Gln Gly Leu Glu Trp Met
            35                  40                  45
```

Gly Trp Met Asn Pro Asn Ser Ala Asn Pro Gly Tyr Ala Gln Lys Phe
            50                  55                  60

Gln Gly Arg Val Thr Met Thr Arg Asn Thr Ser Ile Ser Thr Ala Phe
 65                  70                  75                  80

Met Glu Leu Ser Ser Leu Arg Ser Asp Asp Thr Ala Val Tyr Tyr Cys
                 85                  90                  95

Ala Arg Ala Arg Val Thr Ile His Tyr Asp Ile Leu Thr Gly Tyr Tyr
            100                 105                 110

Ser Asn Ala Phe Asp Ile Trp Gly Gln Gly Thr Met Val Ala Val Ser
        115                 120                 125

Ser

<210> SEQ ID NO 8
<211> LENGTH: 108
<212> TYPE: PRT
<213> ORGANISM: Artificial Sequence
<220> FEATURE:
<223> OTHER INFORMATION: Synthetic

<400> SEQUENCE: 8

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Thr Ile Ser Ser Tyr
             20                  25                  30

Leu Asn Trp Tyr Gln Gln Lys Pro Gly Lys Ala Pro Lys Leu Leu Ile
         35                  40                  45

Tyr Ala Ala Ser Ser Leu Gln Ser Gly Val Pro Ser Arg Phe Ser Gly
     50                  55                  60

Ser Gly Ser Gly Ala Asp Phe Thr Leu Thr Ile Ser Ser Leu Gln Pro
 65                  70                  75                  80

Glu Asp Phe Ala Thr Tyr Tyr Cys Gln Gln Ser Tyr Thr Thr Phe Met
                 85                  90                  95

Tyr Thr Phe Gly Gln Gly Thr Met Leu Glu Ile Lys
            100                 105

<210> SEQ ID NO 9
<211> LENGTH: 387
<212> TYPE: DNA
<213> ORGANISM: Artificial Sequence
<220> FEATURE:
<223> OTHER INFORMATION: Synthetic

<400> SEQUENCE: 9
caagtgcagc tggtgcagtc tggggctgag gtgaagaagc ctggggcctc agtgaaggtc      60
tcctgcaagg cttctggata caccttcacc agttatgata tcaactgggt gcgacaggcc     120
tctggacaag ggcttgagtg gatgggatgg atgaacccta acagtgctaa cccaggctat     180
gcacagaagt tccagggcag agtcaccatg accaggaaca cctccataag cacagccttc     240
atggagctga gcagcctgag atctgacgac acggccgtgt attactgtgc gagagcccga     300
gtaactatac attacgatat tttgactggt tattattcga atgcttttga tatctggggc     360
caagggacaa tggtcgccgt ctcttca                                         387

<210> SEQ ID NO 10
<211> LENGTH: 324
<212> TYPE: DNA
<213> ORGANISM: Artificial Sequence
<220> FEATURE:

<223> OTHER INFORMATION: Synthetic

<400> SEQUENCE: 10

```
gacatccaga tgacccagtc tccatcctcc ctgtctgcat ctgtaggaga cagagtcacc      60
atcacttgcc gggcaagtca gaccattagc agctatttaa attggtatca gcagaaacca     120
gggaaagccc ctaagctcct gatctatgct gcatccagtt tgcaaagtgg ggtcccatca     180
aggttcagtg gcagtggatc tggggcagat ttcactctca ccatcagcag tctgcaacct     240
gaagattttg caacttacta ctgtcaacag agttacacta ccttcatgta cacttttggc     300
caggggacca tgctggagat caaa                                            324
```

<210> SEQ ID NO 11
<211> LENGTH: 5
<212> TYPE: PRT
<213> ORGANISM: Artificial Sequence
<220> FEATURE:
<223> OTHER INFORMATION: Synthetic

<400> SEQUENCE: 11

Ser Tyr Ala Ile Ser
1               5

<210> SEQ ID NO 12
<211> LENGTH: 17
<212> TYPE: PRT
<213> ORGANISM: Artificial Sequence
<220> FEATURE:
<223> OTHER INFORMATION: Synthetic

<400> SEQUENCE: 12

Gly Ile Ile Pro Ile Phe Gly Thr Thr Asn Tyr Ala Gln Lys Phe Gln
1               5                   10                  15

Gly

<210> SEQ ID NO 13
<211> LENGTH: 13
<212> TYPE: PRT
<213> ORGANISM: Artificial Sequence
<220> FEATURE:
<223> OTHER INFORMATION: Synthetic

<400> SEQUENCE: 13

Arg Ser Ala Tyr Gly Asp Lys Gly Tyr Tyr Phe Asp Tyr
1               5                   10

<210> SEQ ID NO 14
<211> LENGTH: 11
<212> TYPE: PRT
<213> ORGANISM: Artificial Sequence
<220> FEATURE:
<223> OTHER INFORMATION: Synthetic

<400> SEQUENCE: 14

Arg Ala Ser Gln Ser Val Ser Asn Phe Leu Ala
1               5                   10

<210> SEQ ID NO 15
<211> LENGTH: 7
<212> TYPE: PRT
<213> ORGANISM: Artificial Sequence
<220> FEATURE:
<223> OTHER INFORMATION: Synthetic

<400> SEQUENCE: 15

Asp Ala Ser Asn Arg Ala Thr
1               5

<210> SEQ ID NO 16
<211> LENGTH: 11
<212> TYPE: PRT
<213> ORGANISM: Artificial Sequence
<220> FEATURE:
<223> OTHER INFORMATION: Synthetic

<400> SEQUENCE: 16

Gln Gln Arg Ser Asn Trp Pro Pro Gln Glu Thr
1               5                   10

<210> SEQ ID NO 17
<211> LENGTH: 122
<212> TYPE: PRT
<213> ORGANISM: Artificial Sequence
<220> FEATURE:
<223> OTHER INFORMATION: Synthetic

<400> SEQUENCE: 17

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Thr Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Asn Ser Leu Arg Ser Glu Asp Thr Ala Val Tyr Tyr Cys
                85                  90                  95

Ala Gly Arg Ser Ala Tyr Gly Asp Lys Gly Tyr Tyr Phe Asp Tyr Trp
            100                 105                 110

Gly Gln Gly Thr Leu Val Thr Val Ser Ser
        115                 120

<210> SEQ ID NO 18
<211> LENGTH: 109
<212> TYPE: PRT
<213> ORGANISM: Artificial Sequence
<220> FEATURE:
<223> OTHER INFORMATION: Synthetic

<400> SEQUENCE: 18

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Asn Phe
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Val Tyr Tyr Cys Gln Gln Arg Ser Asn Trp Pro Pro
                85                  90                  95

Gln Glu Thr Phe Gly Gln Gly Thr Lys Val Glu Ile Lys
            100                 105

<210> SEQ ID NO 19
<211> LENGTH: 366
<212> TYPE: DNA
<213> ORGANISM: Artificial Sequence
<220> FEATURE:
<223> OTHER INFORMATION: Synthetic

<400> SEQUENCE: 19
caggtgcagc tggtgcagtc tggggctgag gtgaagaagc ctgggtcgtc ggtgaaggtc      60
tcctgcaagg cttctggagg caccttcagc agctatgcta tcagctgggt gcgacaggcc     120
cctggacaag ggcttgagtg gatgggaggg atcatcccta tctttggtac aaacaaactac    180 gcacagaagt tccagggcag agtcacgatt accgcggacg aatccacgag cacagcctac     240
atggagctga acagcctgag atctgaggac acggccgtgt attactgtgc gggacgttcg     300
gcctacggtg ataaagggta ctactttgat tactggggcc agggaaccct ggtcaccgtc     360
tcctca                                                                 366

<210> SEQ ID NO 20
<211> LENGTH: 327
<212> TYPE: DNA
<213> ORGANISM: Artificial Sequence
<220> FEATURE:
<223> OTHER INFORMATION: Synthetic

<400> SEQUENCE: 20
gaaattgtgt tgacacagtc tccagccacc ctgtctttgt ctccagggga aagagccacc      60
ctctcctgca gggccagtca gagtgttagc aacttcttag cctggtacca acagaaacct     120
ggccaggctc ccaggctcct catctatgat gcatccaaca gggccactgg catcccagcc     180
aggttcagtg gcagtgggtc tgggacagac ttcactctca ccatcagcag cctacagcct     240
gaagattttg cagtttatta ctgtcagcag cgtagcaact ggcctccgca agagacgttc     300
ggccaaggga ccaaggtgga aatcaaa                                          327

<210> SEQ ID NO 21
<211> LENGTH: 5
<212> TYPE: PRT
<213> ORGANISM: Artificial Sequence
<220> FEATURE:
<223> OTHER INFORMATION: Synthetic

<400> SEQUENCE: 21

Ser Tyr Ala Ile Thr
1               5

<210> SEQ ID NO 22
<211> LENGTH: 17
<212> TYPE: PRT
<213> ORGANISM: Artificial Sequence
<220> FEATURE:
<223> OTHER INFORMATION: Synthetic

<400> SEQUENCE: 22

Gly Ile Ile Pro Ile Phe Gly Thr Ala Asn Phe Ala Gln Lys Phe Gln
1               5                   10                  15

Gly

<210> SEQ ID NO 23

```
<211> LENGTH: 10
<212> TYPE: PRT
<213> ORGANISM: Artificial Sequence
<220> FEATURE:
<223> OTHER INFORMATION: Synthetic

<400> SEQUENCE: 23

Leu Gly Gly Phe Ala Asp Pro Phe Asp Tyr
1               5                   10

<210> SEQ ID NO 24
<211> LENGTH: 11
<212> TYPE: PRT
<213> ORGANISM: Artificial Sequence
<220> FEATURE:
<223> OTHER INFORMATION: Synthetic

<400> SEQUENCE: 24

Arg Ala Ser Gln Ser Val Ser Asn Tyr Leu Ala
1               5                   10

<210> SEQ ID NO 25
<211> LENGTH: 7
<212> TYPE: PRT
<213> ORGANISM: Artificial Sequence
<220> FEATURE:
<223> OTHER INFORMATION: Synthetic

<400> SEQUENCE: 25

Asp Ala Phe Asn Arg Ala Thr
1               5

<210> SEQ ID NO 26
<211> LENGTH: 11
<212> TYPE: PRT
<213> ORGANISM: Artificial Sequence
<220> FEATURE:
<223> OTHER INFORMATION: Synthetic

<400> SEQUENCE: 26

Gln Gln Arg Ser Asn Trp Pro Pro Arg Ile Thr
1               5                   10

<210> SEQ ID NO 27
<211> LENGTH: 119
<212> TYPE: PRT
<213> ORGANISM: Artificial Sequence
<220> FEATURE:
<223> OTHER INFORMATION: Synthetic

<400> SEQUENCE: 27

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Thr Trp Val Arg Gln Ala Pro Gly Gln Gly Leu Glu Trp Met
        35                  40                  45

Gly Gly Ile Ile Pro Ile Phe Gly Thr Ala Asn Phe Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala His Leu Gly Gly Phe Ala Asp Pro Phe Asp Tyr Trp Gly Gln Gly
```

```
                    100                 105                 110
Thr Leu Val Thr Val Ser Ser
            115

<210> SEQ ID NO 28
<211> LENGTH: 109
<212> TYPE: PRT
<213> ORGANISM: Artificial Sequence
<220> FEATURE:
<223> OTHER INFORMATION: Synthetic

<400> SEQUENCE: 28

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Asn Tyr
            20                  25                  30

Leu Ala Trp Tyr Gln Gln Lys Ala Gly Gln Ala Pro Arg Val Leu Ile
        35                  40                  45

Tyr Asp Ala Phe Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Arg Ile Thr Phe Gly Gln Gly Thr Arg Leu Glu Ile Lys
            100                 105

<210> SEQ ID NO 29
<211> LENGTH: 357
<212> TYPE: DNA
<213> ORGANISM: Artificial Sequence
<220> FEATURE:
<223> OTHER INFORMATION: Synthetic

<400> SEQUENCE: 29
caggtgcagc tggtgcagtc tggggctgag gtgaagaagc ctgggtcctc ggtgaaggtc      60
tcctgcaagg cttctggagg caccttcagc agctatgcta tcacctgggt gcgacaggcc    120
cctggacaag gcttgagtg gatgggaggg atcatcccta tctttggtac agcaaacttc     180
gcacagaagt tccagggcag agtcacgatt accgcggacg aatccacgag cacagcctac    240
atggagctga gcagcctgag atctgaggac acggccgtgt attactgtgc ccacctaggg    300
gggttcgctg accccttga ctactggggc cagggaaccc tggtcaccgt ctcctca       357

<210> SEQ ID NO 30
<211> LENGTH: 327
<212> TYPE: DNA
<213> ORGANISM: Artificial Sequence
<220> FEATURE:
<223> OTHER INFORMATION: Synthetic

<400> SEQUENCE: 30
gaaattgtgt tgacacagtc tccagccacc ctgtctttgt ctccagggga aagagccacc     60
ctctcctgca gggccagtca gagtgttagc aactacttag cctggtacca acagaaagct    120
ggccaggctc ccagggtcct catctatgat gcattcaaca gggccactgg catcccagcc    180
aggttcagtg gcagtgggtc tgggacagac ttcactctca ccatcagcag cctagagcct    240
```

```
gaagattttg cagtttatta ctgtcagcag cgtagcaact ggcctccgcg gatcaccttc    300
ggccaaggga cacgactgga gattaaa                                         327
```

ANTI-SARS-COV-2 NEUTRALIZING ANTIBODIES

CROSS-REFERENCE TO RELATED APPLICATIONS

This application claims priority from PCT Patent Application No. PCT/CN2020/113404 filed on Sep. 4, 2020. The PCT Patent Application is hereby expressly incorporated by reference herein in its entirety.

REFERENCE TO AN ELECTRONIC SEQUENCE LISTING

The instant application contains a Sequence Listing which has been submitted electronically in ASCII format and is herein incorporated by reference in its entirety. Said ASCII copy, created on Aug. 2, 2021, is named SequenceListing.txt and is 14 KB in size.

FIELD OF THE INVENTION

The present disclosure generally relates to novel anti-SARS-COV-2 neutralizing antibodies.

BACKGROUND

The global pandemic of the coronavirus disease 2019 (COVID-19) caused by a new coronavirus, i.e. severe acute respiratory syndrome coronavirus 2 (SARS-CoV-2), has severely deteriorated public health and economy. While majority of the infected population showed mild symptoms, some progressed to acute respiratory distress syndrome and more than 700,000 deaths have been reported to date.

The infection of SARS-CoV-2 to a host cell is mediated by a glycoprotein expressed on the virus envelope named a spike (S) glycoprotein, which comprises S1 subunit and S2 subunit. The S1 subunit contains the receptor-binding domain (RBD) that directly binds to the human angiotensin converting enzyme 2 (ACE2) receptor on the host cell, while the S2 subunit mediates the fusion of the virus envelope with the host cell membrane so as to facilitate the infection of the virus.

Convalescent patients' plasma has been used to treat other infections and has also been proved to be beneficial for both mild and severe COVID-19 patients, due to the neutralizing antibodies produced in plasma. However, convalescent plasma treatment is limited since the plasma was donated by people recovered from COVID-19 and cannot be produced on a large-scale.

Therefore, there is an urgent need for large-scale neutralizing antibodies with highly potent neutralizing effects against SARS-COV-2.

SUMMARY OF THE INVENTION

Throughout the present disclosure, the articles "a", "an", and "the" are used herein to refer to one or to more than one (i.e., to at least one) of the grammatical object of the article. By way of example, "an antibody" means one antibody or more than one antibody.

In one respect, the present disclosure provides an isolated or recombinant antibody or an antigen-binding fragment thereof capable of specifically binding to SARS-CoV-2, comprising:

a) 1, 2, or 3 heavy chain CDR (VH-CDR) sequences selected from SEQ ID NO: 1, SEQ ID NO: 2, and SEQ ID NO: 3;
b) 1, 2, or 3 heavy chain CDR sequences selected from SEQ ID NO: 11, SEQ ID NO: 12, and SEQ ID NO: 13; or
c) 1, 2, or 3 heavy chain CDR sequences selected from SEQ ID NO: 21, SEQ ID NO: 22, and SEQ ID NO: 23.

In some embodiments, the antibody or antigen-binding fragment thereof further comprising:

a) 1, 2, or 3 light chain CDR (VL-CDR) sequences selected from SEQ ID NO: 4, SEQ ID NO: 5, and SEQ ID NO: 6;
b) 1, 2, or 3 light chain CDR sequences selected from SEQ ID NO: 14, SEQ ID NO: 15, and SEQ ID NO: 16; or
c) 1, 2, or 3 light chain CDR sequences selected from SEQ ID NO: 24, SEQ ID NO: 25, and SEQ ID NO: 26.

In some embodiments, the antibody or antigen binding fragment comprising:

a) the VH-CDR1, the VH-CDR2, and the VH-CDR3 comprise amino acid sequences of SEQ ID NO: 1, SEQ ID NO: 2, and SEQ ID NO: 3, respectively, and the VL-CDR1, the VL-CDR2, and the VL-CDR3 comprise amino acid sequences of SEQ ID NO: 4, SEQ ID NO: 5, and SEQ ID NO: 6, respectively;
b) the VH-CDR1, the VH-CDR2, and the VH-CDR3 comprise amino acid sequences of SEQ ID NO: 11, SEQ ID NO: 12, and SEQ ID NO: 13, respectively, and the VL-CDR1, the VL-CDR2, and the VL-CDR3 comprise amino acid sequences of SEQ ID NO: 14, SEQ ID NO: 15, and SEQ ID NO: 16, respectively; or
c) the VH-CDR1, the VH-CDR2, and the VH-CDR3 comprise amino acid sequences of SEQ ID NO: 21, SEQ ID NO: 22, and SEQ ID NO: 23, respectively, and the VL-CDR1, the VL-CDR2, and the VL-CDR3 comprise amino acid sequences of SEQ ID NO: 24, SEQ ID NO: 25, and SEQ ID NO: 26, respectively.

In some embodiments, the antibody or an antigen-binding fragment thereof comprising a variable heavy chain variable region (VH) comprising an amino acid sequence of SEQ ID NO: 7, SEQ ID NO: 17, SEQ ID NO: 27, or a sequence having at least 80% sequence identity thereof.

In some embodiments, the antibody or an antigen-binding fragment thereof further comprising a light chain variable region (VL) comprising an amino acid sequence of SEQ ID NO: 8, SEQ ID NO: 18, SEQ ID NO: 28, or a sequence having at least 80% sequence identity thereof.

In some embodiments, the antibody or antigen-binding fragment comprising a pair of heavy chain variable region and light chain variable region sequences selected from the group consisting of: SEQ ID NOs: 7/8, 17/18, 27/28, or a pair of homologous sequences thereof having at least 80% sequence identity yet retaining specific binding affinity to SARS-CoV-2.

In some embodiments, the antibody or antigen-binding fragment thereof further comprising one or more amino acid residue mutations yet retaining specific binding to SARS-CoV-2.

In some embodiments, at least one of the mutations is in one or more of the CDR sequences, and/or in one or more of the VH or VL sequences but not in any of the CDR sequences.

In some embodiments, the antibody or antigen-binding fragment thereof further comprising a heavy chain constant region and/or a light chain constant region.

In some embodiments, the heavy chain constant region is from human IgG1.

In some embodiments, the antibody or antigen-binding fragment thereof is a diabody, a Fab, a Fab', a F(ab')2, a Fd, an Fv fragment, a disulfide stabilized Fv fragment (dsFv), a (dsFv)$_2$, a bispecific dsFv (dsFv-dsFv'), a disulfide stabilized diabody (ds diabody), a single-chain antibody molecule (scFv), an scFv dimer (bivalent diabody), a multispecific antibody, a camelized single domain antibody, a nanobody, a domain antibody, or a bivalent domain antibody.

In some embodiments, the antibody or antigen-binding fragment thereof is bispecific.

In some embodiments, the antibody or antigen-binding fragment thereof linked to one or more conjugate moieties.

In another aspect, the present disclosure also provides an antibody or an antigen-binding fragment thereof, which competes for binding to SARS-CoV-2 with the above-mentioned antibody or antigen-binding fragment thereof.

In another aspect, the present disclosure also provides a pharmaceutical composition comprising one or more of the above-mentioned antibody or antigen-binding fragment thereof, and a pharmaceutically acceptable carrier.

In some embodiments, the pharmaceutical composition further comprising a second antibody capable of neutralizing SARS-CoV-2.

In some embodiments, the second antibody binding to SARS-CoV-2 at an epitope distinct from that/those bound by the above-mentioned antibodies or antigen-binding fragments thereof.

In another aspect, the present disclosure also provides a method of treating or preventing SARS-CoV-2 infection in a subject, comprising administering to the subject an effective amount of the above-mentioned antibody or antigen-binding fragment thereof or the above-mentioned pharmaceutical composition.

In some embodiments, the subject is human or non-human animal.

In some embodiments, the subject has been identified as having SARS-CoV-2 infection, or is suspected of having SARS-CoV-2 infection, or is at risk of exposure to SARS-CoV-2.

In some embodiments, the administration is via oral, nasal, intravenous, subcutaneous, sublingual, or intramuscular administration.

In some embodiments, the method further comprises administering an effective amount of a second therapeutic agent.

In some embodiments, the second therapeutic agent is selected from an antiviral agent (such as a second SARS-CoV-2 neutralizing antibody), RNA dependent RNA polymerase inhibitor, a nucleoside analog, antiviral cytokines (such as interferons), or immunostimulatory agents.

In another aspect, the present disclosure also provides a method of neutralizing SARS-CoV-2 in a subject, comprising administering the above-mentioned antibody or antigen-binding fragment thereof of or the above-mentioned pharmaceutical composition to the subject.

In another aspect, the present disclosure also provides a method for preventing or reducing transmission of SARS-CoV-2 by a SARS-CoV-2 infected subject, comprising administering to the SARS-CoV-2 infected subject an effective amount of the above-mentioned antibody or antigen-binding fragment thereof, or the above-mentioned pharmaceutical composition.

In another aspect, the present disclosure also provides a method of reducing viral load in a SARS-CoV-2 infected subject, comprising administering to the subject an effective amount of the above-mentioned antibody or antigen-binding fragment thereof, or the above-mentioned pharmaceutical composition.

In another aspect, the present disclosure also provides use of the above-mentioned antibody or antigen-binding fragment thereof in the manufacture of a medicament for treating or preventing SARS-CoV-2 infection in a subject; or for preventing, inhibiting progression of, and/or delaying the onset of SARS-CoV-2 infection or an SARS-CoV-2-associated condition in a subject; or for preventing or reducing transmission of SARS-CoV-2 by a SARS-CoV-2 infected subject; or for reducing viral load in a SARS-CoV-2 infected subject.

In another aspect, the present disclosure also provides a kit comprising the above-mentioned antibody or antigen-binding fragment thereof or the above-mentioned pharmaceutical composition, useful in detecting SARS-CoV-2 presence.

In another aspect, the present disclosure provides an isolated polynucleotide encoding the antibody or antigen binding fragment thereof as described herein.

In some embodiments, the isolated polynucleotide of the present disclosure comprises a nucleotide sequence selected from a group consisting of: SEQ ID NOs: 9-10, 19-20 and 29-30, or a homologous sequence thereof having at least 80% sequence identity.

In some embodiments, the homologue sequence encodes the same protein as encoded by any nucleotide sequence selected from the group consisting of SEQ ID NOs: 9-10, 19-20 and 29-30.

DETAILED DESCRIPTION OF THE INVENTION

Figure 1:
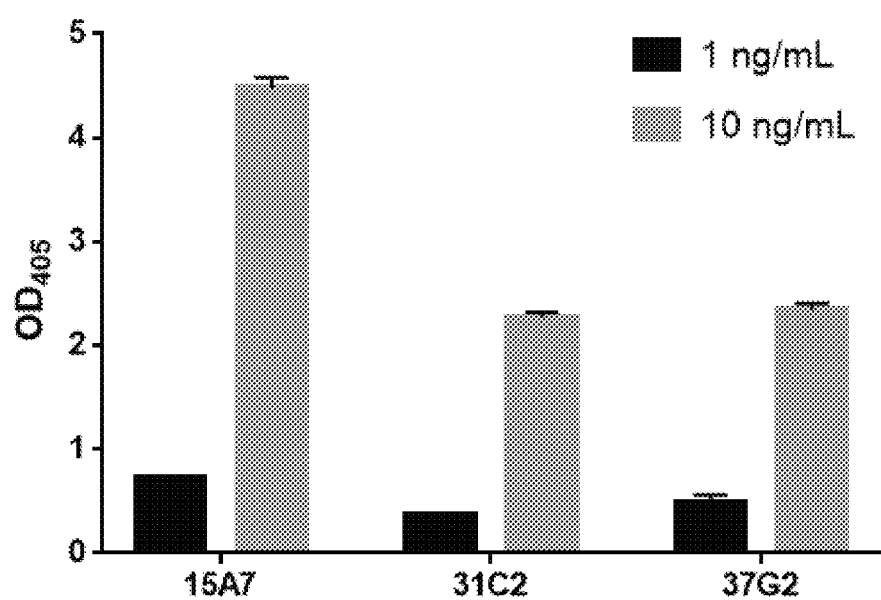
FIG. 1 shows binding profile of the antibodies provided in the disclosure with SARS-CoV-2 virus-like particles (VLP) as determined by ELISA.

The following description of the disclosure is merely intended to illustrate various embodiments of the disclosure. As such, the specific modifications discussed are not to be construed as limitations on the scope of the disclosure. It will be apparent to a person skilled in the art that various equivalents, changes, and modifications may be made without departing from the scope of the disclosure, and it is understood that such equivalent embodiments are to be included herein. All references cited herein, including publications, patents and patent applications are incorporated herein by reference in their entirety.

Definitions

The term "antibody" as used herein includes any immunoglobulin, monoclonal antibody, polyclonal antibody, multivalent antibody, bivalent antibody, monovalent antibody, multispecific antibody, or bispecific antibody that binds to a specific antigen. A native intact antibody comprises two heavy (H) chains and two light (L) chains. Mammalian heavy chains are classified as alpha, delta, epsilon, gamma, and mu, each heavy chain consists of a variable region (VH)

and a first, second, third, and optionally fourth constant region (CH1, CH2, CH3, CH4 respectively); mammalian light chains are classified as λ or κ, while each light chain consists of a variable region (VL) and a constant region. The antibody has a "Y" shape, with the stem of the Y consisting of the second and third constant regions of two heavy chains bound together via disulfide bonding. Each arm of the Y includes the variable region and first constant region of a single heavy chain bound to the variable and constant regions of a single light chain. The variable regions of the light and heavy chains are responsible for antigen binding. The variable regions in both chains generally contain three highly variable loops called the complementarity determining regions (CDRs) (light chain CDRs including VL-CDR1, VL-CDR2, and VL-CDR3, heavy chain CDRs including VH-CDR1, VH-CDR2, VH-CDR3). CDR boundaries for the antibodies and antigen-binding fragments disclosed herein may be defined or identified by the conventions of Kabat, IMGT, Chothia, or Al-Lazikani (Al-Lazikani, B., Chothia, C., Lesk, A. M., *J. Mol. Biol.*, 273(4), 927 (1997); Chothia, C. et al., *J Mol Biol.* December 5; 186(3):651-63 (1985); Chothia, C. and Lesk, A. M., *J. Mol. Biol.*, 196,901 (1987); Chothia, C. et al., *Nature.* December 21-28; 342 (6252):877-83 (1989); Kabat E. A. et al., Sequences of Proteins of immunological Interest, 5th Ed. Public Health Service, National Institutes of Health, Bethesda, Md. (1991); Marie-Paule Lefranc et al., *Developmental and Comparative Immunology*, 27: 55-77 (2003); Marie-Paule Lefranc et al., *Immunome Research*, 1(3), (2005); Marie-Paule Lefranc, Molecular Biology of B cells (second edition), chapter 26, 481-514, (2015)). The three CDRs are interposed between flanking stretches known as framework regions (FRs) (light chain FRs including LFR1, LFR2, LFR3, and LFR4, heavy chain FRs including HFR1, HFR2, HFR3, and HFR4), which are more highly conserved than the CDRs and form a scaffold to support the highly variable loops. The constant regions of the heavy and light chains are not involved in antigen-binding, but exhibit various effector functions. Antibodies are assigned to classes based on the amino acid sequences of the constant regions of their heavy chains. The five major classes or isotypes of antibodies are large immunoglobulin A (IgA), IgD, IgE, IgG, and IgM, which are characterized by the presence of alpha, delta, epsilon, gamma, and mu heavy chains, respectively. Several of the major antibody classes are divided into subclasses such as IgG1 (gamma1 heavy chain), IgG2 (gamma2 heavy chain), IgG3 (gamma3 heavy chain), IgG4 (gamma4 heavy chain), IgA1 (alpha1 heavy chain), or IgA2 (alpha2 heavy chain).

In certain embodiments, the antibody provided herein encompasses any antigen-binding fragments thereof. The term "antigen-binding fragment" as used herein refers to an antibody fragment formed from a portion of an antibody comprising one or more CDRs, or any other antibody fragment that binds to an antigen but does not comprise an intact native antibody structure. Examples of antigen-binding fragments include, without limitation, a diabody, a Fab, a Fab', a F(ab')$_2$, an Fv fragment, a disulfide stabilized Fv fragment (dsFv), a (dsFv)$_2$, a bispecific dsFv (dsFv-dsFv'), a disulfide stabilized diabody (ds diabody), a single-chain antibody molecule (scFv), an scFv dimer (bivalent diabody), a bispecific antibody, a multispecific antibody, a camelized single domain antibody, a nanobody, a domain antibody, and a bivalent domain antibody. An antigen-binding fragment is capable of binding to the same antigen to which the parent antibody binds.

"Fab" with regard to an antibody refers to that portion of the antibody consisting of a single light chain (both variable and constant regions) bound to the variable region and first constant region of a single heavy chain by a disulfide bond.

"Fab'" refers to a Fab fragment that includes a portion of the hinge region.

"F(ab')$_2$" refers to a dimer of Fab'.

"Fc" with regard to an antibody (e.g. of IgG, IgA, or IgD isotype) refers to that portion of the antibody consisting of the second and third constant domains of a first heavy chain bound to the second and third constant domains of a second heavy chain via disulfide bonding. Fc with regard to antibody of IgM and IgE isotype further comprises a fourth constant domain. The Fc portion of the antibody is responsible for various effector functions such as antibody-dependent cell-mediated cytotoxicity (ADCC), and complement dependent cytotoxicity (CDC), but does not function in antigen binding.

"Fv" with regard to an antibody refers to the smallest fragment of the antibody to bear the complete antigen binding site. An Fv fragment consists of the variable region of a single light chain bound to the variable region of a single heavy chain.

"Single-chain Fv antibody" or "scFv" refers to an engineered antibody consisting of a light chain variable region and a heavy chain variable region connected to one another directly or via a peptide linker sequence (Huston J S et al. *Proc Natl Acad Sci USA*, 85:5879(1988)).

"Single-chain Fv-Fc antibody" or "scFv-Fc" refers to an engineered antibody consisting of a scFv connected to the Fc region of an antibody.

"Camelized single domain antibody", "heavy chain antibody", or "HCAb" refers to an antibody that contains two $V_H$ domains and no light chains (Riechmann L. and Muyldermans S., *J Immunol Methods.* December 10; 231(1-2):25-38 (1999); Muyldermans S., *J Biotechnol.* June; 74(4):277-302 (2001); WO94/04678; WO94/25591; U.S. Pat. No. 6,005,079). Heavy chain antibodies were originally derived from Camelidae (camels, dromedaries, and llamas). Although devoid of light chains, camelized antibodies have an authentic antigen-binding repertoire (Hamers-Casterman C. et al., *Nature.* Jun. 3; 363(6428):446-8 (1993); Nguyen V K. et al. *Immunogenetics.* April; 54(1):39-47 (2002); Nguyen V K. et al. *Immunology.* May; 109(1):93-101 (2003)). The variable domain of a heavy chain antibody (VHH domain) represents the smallest known antigen-binding unit generated by adaptive immune responses (Koch-Nolte F. et al., *FASEB J.* November; 21(13):3490-8. Epub 2007 Jun. 15 (2007)).

A "nanobody" refers to an antibody fragment that consists of a VHH domain from a heavy chain antibody and two constant domains, CH2 and CH3.

A "diabody" or "dAb" includes small antibody fragments with two antigen-binding sites, wherein the fragments comprise a $V_H$ domain connected to a $V_L$ domain in the same polypeptide chain ($V_H$-$V_L$ or $V_L$-$V_H$) (see, e.g. Holliger P. et al., *Proc Natl Acad Sci USA*. July 15; 90(14):6444-8 (1993); EP404097; WO93/11161). By using a linker that is too short to allow pairing between the two domains on the same chain, the domains are forced to pair with the complementary domains of another chain, thereby creating two antigen-binding sites. The antigen-binding sites may target the same or different antigens (or epitopes). In certain embodiments, a "bispecific ds diabody" is a diabody target two different antigens (or epitopes).

A "domain antibody" refers to an antibody fragment containing only the variable region of a heavy chain or the variable region of a light chain. In certain instances, two or more $V_H$ domains are covalently joined with a peptide linker to create a bivalent or multivalent domain antibody. The two $V_H$ domains of a bivalent domain antibody may target the same or different antigens.

The term "valent" as used herein refers to the presence of a specified number of antigen binding sites in a given molecule. The term "monovalent" refers to an antibody or an antigen-binding fragment having only one single antigen-binding site; and the term "multivalent" refers to an antibody or antigen-binding fragment having multiple antigen-binding sites. As such, the terms "bivalent", "tetravalent", and "hexavalent" denote the presence of two binding sites, four binding sites, and six binding sites, respectively, in an antigen-binding molecule. In some embodiments, the antibody or antigen-binding fragment thereof is bivalent.

As used herein, a "bispecific" antibody refers to an artificial antibody which has fragments derived from two different monoclonal antibodies and is capable of binding to two different epitopes. The two epitopes may present on the same antigen, or they may present on two different antigens.

In certain embodiments, an "scFv dimer" is a bivalent diabody or bispecific scFv (BsFv) comprising $V_H$-$V_L$ (linked by a peptide linker) dimerized with another $V_H$-$V_L$ moiety such that $V_H$'s of one moiety coordinate with the $V_L$'s of the other moiety and form two binding sites which can target the same antigens (or epitopes) or different antigens (or epitopes). In other embodiments, an "scFv dimer" is a bispecific diabody comprising $V_{H1}$-$V_{L2}$ (linked by a peptide linker) associated with $V_{L1}$-$V_{H2}$ (also linked by a peptide linker) such that $V_{H1}$ and $V_{L1}$ coordinate and $V_{H2}$ and $V_{L2}$ coordinate and each coordinated pair has a different antigen specificity.

A "dsFv" refers to a disulfide-stabilized Fv fragment that the linkage between the variable region of a single light chain and the variable region of a single heavy chain is a disulfide bond. In some embodiments, a "(dsFv)$_2$" or "(dsFv-dsFv')" comprises three peptide chains: two $V_H$ moieties linked by a peptide linker (e.g. a long flexible linker) and bound to two $V_L$ moieties, respectively, via disulfide bridges. In some embodiments, dsFv-dsFv' is bispecific in which each disulfide paired heavy and light chain has a different antigen specificity.

The term "chimeric" as used herein, means an antibody or antigen-binding fragment, having a portion of heavy and/or light chain derived from one species, and the rest of the heavy and/or light chain derived from a different species. In some embodiments, the non-human animal is a mammal, for example, a mouse, a rat, a rabbit, a goat, a sheep, a guinea pig, or a hamster.

The term "affinity" as used herein refers to the strength of non-covalent interaction between an immunoglobulin molecule (i.e. antibody) or fragment thereof and an antigen.

The term "specific binding" or "specifically binds" as used herein refers to a non-random binding reaction between two molecules, such as for example between an antibody and an antigen. Specific binding can be characterized in binding affinity, for example, represented by $K_D$ value, i.e., the ratio of dissociation rate to association rate ($k_{off}/k_{on}$) when the binding between the antigen and antigen-binding molecule reaches equilibrium. $K_D$ may be determined by using any conventional method known in the art, including but are not limited to surface plasmon resonance method, Octet method, microscale thermophoresis method, HPLC-MS method and FACS assay method. A $K_D$ value of $\leq 10^{-6}$ M (e.g. $\leq 5 \times 10^{-7}$ M, $\leq 2 \times 10^{-7}$ M, $\leq 10^{-7}$ M, $\leq 5 \times 10^{-8}$ M, $\leq 2 \times 10^{-8}$ M, $\leq 10^{-8}$ M, $\leq 5 \times 10^{-9}$ M, $\leq 4 \times 10^{-9}$ M, $\leq 3 \times 10^{-9}$ M, $\leq 2 \times 10^{-9}$ M, or $\leq 10^{-9}$ M) can indicate specific binding between an antibody or antigen binding fragments thereof and SARS-CoV-2 (e.g. SARS-CoV-2).

The term "epitope" as used herein refers to the specific group of atoms or amino acids on an antigen to which an antibody binds. Two antibodies may bind the same or a closely related epitope within an antigen if they exhibit competitive binding for the antigen. An epitope can be linear or conformational (i.e. including amino acid residues spaced apart). For example, if an antibody or antigen-binding fragment blocks binding of a reference antibody to the antigen by at least 85%, or at least 90%, or at least 95%, then the antibody or antigen-binding fragment may be considered to bind the same/closely related epitope as the reference antibody.

The term "amino acid" as used herein refers to an organic compound containing amine (—NH$_2$) and carboxyl (—COOH) functional groups, along with a side chain specific to each amino acid. The names of amino acids are also represented as standard single letter or three-letter codes in the present disclosure, which are summarized as follows.

| Names | Three-letter Code | Single-letter Code |
|---|---|---|
| Alanine | Ala | A |
| Arginine | Arg | R |
| Asparagine | Asn | N |
| Aspartic acid | Asp | D |
| Cysteine | Cys | C |
| Glutamic acid | Glu | E |
| Glutamine | Gln | Q |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

A "conservative substitution" with reference to amino acid sequence refers to replacing an amino acid residue with a different amino acid residue having a side chain with similar physiochemical properties. For example, conservative substitutions can be made among amino acid residues with hydrophobic side chains (e.g. Met, Ala, Val, Leu, and Ile), among residues with neutral hydrophilic side chains (e.g. Cys, Ser, Thr, Asn and Gln), among residues with acidic side chains (e.g. Asp, Glu), among amino acids with basic side chains (e.g. His, Lys, and Arg), or among residues with aromatic side chains (e.g. Trp, Tyr, and Phe). As known in the art, conservative substitution usually does not cause significant change in the protein conformational structure, and therefore could retain the biological activity of a protein.

"Percent (%) sequence identity" with respect to amino acid sequence (or nucleic acid sequence) is defined as the percentage of amino acid (or nucleic acid) residues in a candidate sequence that are identical to the amino acid (or nucleic acid) residues in a reference sequence, after aligning the sequences and, if necessary, introducing gaps, to achieve the maximum number of identical amino acids (or nucleic acids). Conservative substitution of the amino acid residues may or may not be considered as identical residues. Alignment for purposes of determining percent amino acid (or nucleic acid) sequence identity can be achieved, for example, using publicly available tools such as BLASTN, BLASTp (available on the website of U.S. National Center for Biotechnology Information (NCBI), see also, Altschul S. F. et al., *J. Mol. Biol.*, 215:403-410 (1990); Stephen F. et al., *Nucleic Acids Res.*, 25:3389-3402 (1997)), ClustalW2 (available on the website of European *Bioinformatics Institute, see also, Higgins D. G. et al., Methods in Enzymology*, 266:383-402 (1996); Larkin M. A. et al., *Bioinformatics* (Oxford, England), 23(21): 2947-8 (2007)), and ALIGN or Megalign (DNASTAR) software. A person skilled in the art may use the default parameters provided by the tool, or may customize the parameters as appropriate for the alignment, such as for example, by selecting a suitable algorithm.

An "isolated" substance has been altered by the hand of man from the natural state. If an "isolated" composition or substance occurs in nature, it has been changed or removed from its original environment, or both. For example, a polynucleotide or a polypeptide naturally present in a living animal is not "isolated," but the same polynucleotide or polypeptide is "isolated" if it has been sufficiently separated from the coexisting materials of its natural state so as to exist in a substantially pure state. An "isolated nucleic acid sequence" refers to the sequence of an isolated nucleic acid molecule. In certain embodiments, an "isolated antibody or an antigen-binding fragment thereof" refers to the antibody or antigen-binding fragments thereof having a purity of at least 60%, 70%, 75%, 80%, 81%, 82%, 83%, 84%, 85%, 86%, 87%, 88%, 89%, 90%, 91%, 92%, 93%, 94%, 95%, 96%, 97%, 98%, 99% as determined by electrophoretic methods (such as SDS-PAGE, isoelectric focusing, capillary electrophoresis), or chromatographic methods (such as ion exchange chromatography or reverse phase HPLC).

The term "subject" includes human and non-human animals. Non-human animals include all vertebrates, e.g., mammals and non-mammals, such as non-human primates, mice, rats, cats, rabbits, sheep, dogs, cows, chickens, amphibians, and reptiles. Except when noted, the terms "patient" or "subject" are used herein interchangeably.

The term "prevent" or "preventing" as used herein includes slowing the onset of a disease, reducing the risk of developing a disease, suppressing or delaying the manifestation or development of symptoms associated with a disease, reducing the severity of a subsequent contraction or development of a disease, ameliorating a related symptom, and inducing immunity to protect against a disease, The term "neutralizing" with respect to an antibody means that the antibody is capable of disrupting a formed viral particle or inhibiting formation of a viral particle or prevention of binding or infection of susceptible cells by a viral particle.

"Treating" or "treatment" of a disease, disorder or condition as used herein includes preventing or alleviating a disease, disorder or condition, slowing the onset or rate of development of a disease, disorder or condition, reducing the risk of developing a disease, disorder or condition, reducing or ending symptoms associated with a disease, disorder or condition, generating a complete or partial regression of a disease, disorder or condition, curing a disease, disorder or condition, or some combination thereof.

The term "pharmaceutically acceptable" indicates that the designated carrier, vehicle, diluent, excipient(s), and/or salt is generally chemically and/or physically compatible with the other ingredients comprising the formulation, and physiologically compatible with the recipient thereof.

Illustrative Neutralizing Antibodies Against SARS-CoV-2

In certain embodiments, the present disclosure provides neutralizing antibodies against SARS-CoV-2 and antigen-binding fragments thereof comprising one or more (e.g. 1, 2, 3, 4, 5, or 6) CDRs comprising the sequences selected from the group consisting of SYDIN (SEQ ID NO: 1), WMNPNSANPGYAQKFQG (SEQ ID NO: 2), ARVTIHYDILTGYYSNAFDI (SEQ ID NO: 3), RASQTISSYLN (SEQ ID NO: 4), AASSLQS (SEQ ID NO: 5), QQSYTTFMYT (SEQ ID NO: 6), SYAIS (SEQ ID NO: 11), GIIPIFGTTNYAQKFQG (SEQ ID NO: 12), RSAYGDKGYYFDY (SEQ ID NO: 13), RASQSVSNFLA (SEQ ID NO: 14), DASNRAT (SEQ ID NO: 15), QQRSNWPPQET (SEQ ID NO: 16), SYAIT (SEQ ID NO: 21), GIIPIFGTANFAQKFQG (SEQ ID NO: 22), LGGFADPFDY (SEQ ID NO: 23), RASQSVSNYLA (SEQ ID NO: 24), DAFNRAT (SEQ ID NO: 25), QQRSNWPPRIT (SEQ ID NO: 26).

Antibody "15A7" as used herein refers to a monoclonal antibody having a heavy chain variable region having the sequence of SEQ ID NO: 7, and a light chain variable region having the sequence of SEQ ID NO: 8.

Antibody "31C2" as used herein refers to a monoclonal antibody having a heavy chain variable region having the sequence of SEQ ID NO: 17, and a light chain variable region having the sequence of SEQ ID NO: 18.

Antibody "37G2" as used herein refers to a monoclonal antibody having a heavy chain variable region having the sequence of SEQ ID NO: 27, and a light chain variable region having the sequence of SEQ ID NO: 28.

In certain embodiments, the present disclosure provides neutralizing antibodies against SARS-CoV-2 and antigen-binding fragments thereof comprising one or more (e.g. 1, 2, 3, 4, 5, or 6) CDR sequences of Antibody 15A7, 31C2, or 37G2.

In certain embodiments, the present disclosure provides neutralizing antibodies against SARS-CoV-2 and antigen-binding fragments thereof comprising VH-CDR1 comprising an amino acid sequence selected from the group consisting of SEQ ID NOs: 1, 11 and 21, VH-CDR2 comprising an amino acid sequence selected from the group consisting of SEQ ID NOs: 2, 12 and 22, and VH-CDR3 comprising an amino acid sequence selected from the group consisting of SEQ ID NOs: 3, 13 and 23, and/or VL-CDR1 comprising an amino acid sequence selected from the group consisting of SEQ ID NOs: 4, 14 and 24, VL-CDR2 comprising an amino acid sequence selected from the group consisting of SEQ ID NOs: 5, 15 and 25, and VL-CDR3 comprising an amino acid sequence selected from the group consisting of 6, 16 and 26.

In certain embodiments, the present disclosure provides neutralizing antibodies against SARS-CoV-2 and antigen-binding fragments thereof comprising a VH-CDR1 comprising the sequence of SEQ ID NO: 1, a VH-CDR2 comprising the sequence of SEQ ID NO: 2, a VH-CDR3 comprising the sequence of SEQ ID NO: 3, and/or a VL-CDR1 comprising the sequence of SEQ ID NO: 4, a VL-CDR2 comprising the sequence of SEQ ID NO: 5, and a VL-CDR3 comprising the sequence of SEQ ID NO: 6.

In certain embodiments, the present disclosure provides neutralizing antibodies against SARS-CoV-2 and antigen-binding fragments thereof comprising a VH-CDR1 comprising the sequence of SEQ ID NO: 11, a VH-CDR2 comprising the sequence of SEQ ID NO: 12, a VH-CDR3 comprising the sequence of SEQ ID NO: 13, and/or a VL-CDR1 comprising the sequence of SEQ ID NO: 14, a VL-CDR2 comprising the sequence of SEQ ID NO: 15, and a VL-CDR3 comprising the sequence of SEQ ID NO: 16.

In certain embodiments, the present disclosure provides neutralizing antibodies against SARS-CoV-2 and antigen-binding fragments thereof comprising a VH-CDR1 comprising the sequence of SEQ ID NO: 21, a VH-CDR2 comprising the sequence of SEQ ID NO: 22, a VH-CDR3 comprising the sequence of SEQ ID NO: 23, and/or a VL-CDR1 comprising the sequence of SEQ ID NO: 24, a VL-CDR2 comprising the sequence of SEQ ID NO: 25, and a VL-CDR3 comprising the sequence of SEQ ID NO: 26.

Table 1 below shows the CDR amino acid sequences of antibodies 15A7, 31C2 and 37G2. The CDR boundaries were defined or identified by the convention of Kabat. Table 2 below shows the heavy chain and light chain variable region amino acid sequences of antibodies 15A7, 31C2 and 37G2. Table 3 below shows the heavy chain and light chain variable region nucleic acid sequences of antibodies 15A7, 31C2 and 37G2.

TABLE 1

CDR amino acid sequences of 3 monoclonal antibodies.

| | | CDR1 | CDR2 | CDR3 |
|---|---|---|---|---|
| 15A7 | VH-CDR | SEQ ID NO: 1<br>SYDIN | SEQ ID NO: 2<br>WMNPNSANPGY<br>AQKFQG | SEQ ID NO: 3<br>ARVTIHYD1LTGY<br>YSNAFDI |
| | VL-CDR | SEQ ID NO: 4<br>RASQTISSYLN | SEQ ID NO: 5<br>AASSLQS | SEQ ID NO: 6<br>QQSYTTFMYT |
| 31C2 | VH-CDR | SEQ ID NO: 11<br>SYAIS | SEQ ID NO: 12<br>GIIPIFGTTNYAQK<br>FQG | SEQ ID NO: 13<br>RSAYGDKGYYFD<br>Y |
| | VL-CDR | SEQ ID NO: 14<br>RASQSVSNFLA | SEQ ID NO: 15<br>DASNRAT | SEQ ID NO: 16<br>QQRSNWPPQET |
| 37G2 | VH-CDR | SEQ ID NO: 21<br>SYAIT | SEQ ID NO: 22<br>GI1PIFGTANFAQK<br>FQG | SEQ ID NO: 23<br>LGGFADPFDY |
| | VL-CDR | SEQ ID NO: 24<br>RASQSVSNYLA | SEQ ID NO: 25<br>DAFNRAT | SEQ ID NO: 26<br>QQRSNWPPRIT |

TABLE 2

Variable region amino acid sequences of 3 monoclonal antibodies.

| | VH | VL |
|---|---|---|
| 15A7 | SEQ ID NO: 7<br>QVQLVQSGAEVKKPGASVK<br>VSCKASGYTFTSYDINWVR<br>QASGQGLEWMGWMNPNSAN<br>PGYAQKFQGRVTMTRNTSI<br>STAFMELSSLRSDDTAVYY<br>CARARVTIHYDILTGYYSN<br>AFDIWGQGTMVAVSS | SEQ ID NO: 8<br>DIQMTQSPSSLSASVGDRV<br>TITCRASQTISSYLNWYQQ<br>KPGKAPKLLIYAASSLQSG<br>VPSRFSGSGSGADFTLTIS<br>SLQPEDFATYYCQQSYTTF<br>MYTFGQGTMLEIK |
| 31C2 | SEQ ID NO: 17<br>QVQLVQSGAEVKKPGSSVK<br>VSCKASGGTFSSYAISWVR<br>QAPGQGLEWMGGIIPIFGT<br>TNYAQKFQGRVTITADEST<br>STAYMELNSLRSEDTAVYY<br>CAGRSAYGDKGYYFDYWGQ<br>GTLVTVSS | SEQ ID NO: 18<br>EIVLTQSPATLSLSPGERA<br>TLSCRASQSVSNFLAWYQQ<br>KPGQAPRLLIYDASNRATG<br>IPARFSGSGSGTDFTLTIS<br>SLQPEDFAVYYCQQRSNWP<br>PQETFGQGTKVEIK |
| 37G2 | SEQ ID NO: 27<br>QVQLVQSGAEVKKPGSSVK<br>VSCKASGGTFSSYAITWVR<br>QAPGQGLEWMGGIIPIFGT<br>ANFAQKFQGRVTITADEST<br>STAYMELSSLRSEDTAVYY<br>CAHLGGFADPFDYWGQGTL<br>VTVSS | SEQ ID NO: 28<br>EIVLTQSPATLSLSPGERA<br>TLSCRASQSVSNYLAWYQQ<br>KAGQAPRVLIYDAFNRATG<br>IPARFSGSGSGTDFTLTIS<br>SLEPEDFAVYYCQQRSNWP<br>PRITFGQGTRLEIK |

TABLE 3

Variable region nucleic acid sequences of 3 monoclonal antibodies.

| | VH | VL |
|---|---|---|
| 15A7 | SEQ ID NO: 9<br>CAAGTGCAGCTGGTGCAGT<br>CTGGGGCTGAGGTGAAGAA<br>GCCTGGGGCCTCAGTGAAG<br>GTCTCCTGCAAGGCTTCTG<br>GATACACCTTCACCAGTTA<br>TGATATCAACTGGGTGCGA<br>CAGGCCTCTGGACAAGGGC<br>TTGAGTGGATGGGATGGAT<br>GAACCCTAACAGTGCTAAC<br>CCAGGCTATGCACAGAAGT<br>TCCAGGGCAGAGTCACCAT<br>GACCAGGAACACCTCCATA<br>AGCACAGCCTTCATGGAGC<br>TGAGCAGCCTGAGATCTGA<br>CGACACGGCCGTGTATTAC<br>TGTGCGAGAGCCCGAGTAA<br>CTATACATTACGATATTTT<br>GACTGGTTATTATTCGAAT<br>GCTTTTGATATCTGGGGCC<br>AAGGGACAATGGTCGCCGT<br>CTCTTCA | SEQ ID NO: 10<br>GACATCCAGATGACCCAGT<br>CTCCATCCTCCCTGTCTGC<br>ATCTGTAGGAGACAGAGTC<br>ACCATCACTTGCCGGGCAA<br>GTCAGACCATTAGCAGCTA<br>TTTAAATTGGTATCAGCAG<br>AAACCAGGGAAAGCCCCTA<br>AGCTCCTGATCTATGCTGC<br>ATCCAGTTTGCAAAGTGGG<br>GTCCCATCAAGGTTCAGTG<br>GCAGTGGATCTGGGGCAGA<br>TTTCACTCTCACCATCAGC<br>AGTCTGCAACCTGAAGATT<br>TTGCAACTTACTACTGTCA<br>ACAGAGTTACACTACCTTC<br>ATGTACACTTTTGGCCAGG<br>GGACCATGCTGGAGATCAA<br>A |
| 31C2 | SEQ ID NO: 19<br>CAGGTGCAGCTGGTGCAGT<br>CTGGGGCTGAGGTGAAGAA<br>GCCTGGCTCGTCGGTGAAG<br>GTCTCCTGCAAGGCTTCtG<br>GAGGCACCTTCAGCAGCTA<br>TGCTATCAGCTGGGTGCGA<br>CAGGCCCCTGGACAAGGGC<br>TTGAGTGGATGGGAGGGAT<br>CATCCCTATCTTTGGTACA<br>ACAAACTACGCACAGAAGT<br>TCCAGGGCAGAGTCACGAT<br>TACCGCGGACGAATCCACG | SEQ ID NO: 20<br>GAAATTGTGTTGACACAGT<br>CTCCAGCCACCCTGTCTTT<br>GTCTCCAGGGGAAAGAGCC<br>ACCCTCTCCTGCAGGGCCA<br>GTCAGAGTGTTAGCAACTT<br>CTTAGCCTGGTACCAACAG<br>AAACCTGGCCAGGCTCCCA<br>GGCTCCTCATCTATGATGC<br>ATCCAACAGGGCCACTGGC<br>ATCCCAGCCAGGTTCAGTG<br>GCAGTGGGTCTGGGACAGA<br>CTTCACTCTCACCATCAGC |

TABLE 3-continued

Variable region nucleic acid sequences of 3 monoclonal antibodies.

| | VH | VL |
|---|---|---|
| | AGCACAGCCTACATGGAGC<br>TGAACAGCCTGAGATCTGA<br>GGACACGGCCGTGTATTAC<br>TGTGCGGGACGTTCGGCCT<br>ACGGTGATAAAGGGTACTA<br>CTTTGATTACTGGGGCCAG<br>GGAACCCTGGTCACCGTCT<br>CCTCA | AGCCTACAGCCTGAAGATT<br>TTGCAGTTTATTACTGTCA<br>GCAGCGTAGCAACTGGCCT<br>CCGCAAGAGACGTTCGGCC<br>AAGGGACCAAGGTGGAAAT<br>CAAA |
| 37G2 | SEQ ID NO: 29<br>CAGGTGCAGCTGGTGCAGT<br>CTGGGGCTGAGGTGAAGAA<br>GCCTGGGTCCTCGGTGAAG<br>GTCTCCTGCAAGGCTTCTG<br>GAGGCACCTTCAGCAGCTA<br>TGCTATCACCTGGGTGCGA<br>CAGGCCCCTGGACAAGGGC<br>TTGAGTGGATGGGAGGGAT<br>CATCCCTATCTTTGGTACA<br>GCAAACTTCGCACAGAAGT<br>TCCAGGGCAGAGTCACGAT<br>TACCGCGGACGAATCCACG<br>AGCACAGCCTACATGGAGC<br>TGAGCAGCCTGAGATCTGA<br>GGACACGGCCGTGTATTAC<br>TGTGCCCACCTAGGGGGGT<br>TCGCTGACCCCTTTGACTA<br>CTGGGGCCAGGGAACCCTG<br>GTCACCGTCTCCTCA | SEQ ID NO: 30<br>GAAATTGTGTTGACACAGT<br>CTCCAGCCACCCTGTCTTT<br>GTCTCCAGGGGAAAGAGCC<br>ACCCTCTCCTGCAGGGCCA<br>GTCAGAGTGTTAGCAACTA<br>CTTAGCCTGGTACCAACAG<br>AAAGCTGGCCAGGCTCCCA<br>GGGTCCTCATCTATGATGC<br>ATTCAACAGGGCCACTGGC<br>ATCCCAGCCAGGTTCAGTG<br>GCAGTGGGTCTGGGACAGA<br>CTTCACTCTCACCATCAGC<br>AGCCTAGAGCCTGAAGATT<br>TTGCAGTTTATTACTGTCA<br>GCAGCGTAGCAACTGGCCT<br>CCGCGGATCACCTTCGCC<br>AAGGGACACGACTGGAGAT<br>TAAA |

CDRs are known to be responsible for antigen binding. However, it has been found that not all of the 6 CDRs are indispensable or unchangeable. In other words, it is possible to replace or change or modify one or more CDRs in neutralizing antibodies 15A7, 31C2 and 37G2, yet substantially retain the specific binding affinity to SARS-CoV-2.

The antibodies and antigen-binding fragments thereof provided herein can comprise suitable framework region (FR) sequences from any species, such as mouse, human, rat, or rabbit, as long as the antibodies and antigen-binding fragments thereof can specifically bind to SARS-CoV-2. In certain embodiments, the CDR sequences provided in Table 1 above are obtained from human antibodies. In certain embodiments, the FR sequence is derived from human.

In some embodiments, the antibodies and antigen-binding fragments thereof provided herein comprise all or a portion of the heavy chain variable domain and/or all or a portion of the light chain variable domain. In one embodiment, the antibodies and antigen-binding fragments thereof provided herein is a single domain antibody which consists of all or a portion of the heavy chain variable domain provided herein. More information of such a single domain antibody is available in the art (see, e.g. U.S. Pat. No. 6,248,516).

In certain embodiments, the antibodies and antigen-binding fragments thereof provided herein further comprise an immunoglobulin (Ig) constant region, which optionally further comprises a heavy chain and/or a light chain constant region. In certain embodiments, the heavy chain constant region comprises CH1, hinge, and/or CH2-CH3 regions (or optionally CH2-CH3-CH4 regions). In certain embodiments, the antibodies and antigen-binding fragments thereof provided herein comprises heavy chain constant regions of human IgG1, IgG2, IgG3, IgG4, IgA1, IgA2 or IgM. In certain embodiments, the antibodies and antigen-binding fragments thereof provided herein comprises heavy chain constant regions of human IgG1. In certain embodiments, the antibodies and antigen-binding fragments thereof provided herein comprises heavy chain constant regions of human IgG4. In certain embodiments, the light chain constant region comprises Cκ or Cλ. The constant region of the antibodies and antigen-binding fragments thereof provided herein may be identical to the wild-type constant region sequence or be different in one or more mutations.

In certain embodiments, the antibodies or the antigen-binding fragments thereof provided herein have different amino acid sequences compared with the antibody created by any animal (e.g., human). In certain embodiments, the antibodies or the antigen-binding fragments thereof provided herein have at least 1, 2, 3, 4, 5, 6, 7, 8, 9, 10, 12, 15, 20, 30, 40, 50, or 60 different amino acids compared with the antibody created by any animal (e.g., human). In certain embodiments, the antibodies or the antigen-binding fragments thereof provided herein have different amino acids in FR regions or Fc regions compared with the antibody created by any animal (e.g., human). In certain embodiments, the antibodies or the antigen-binding fragments thereof provided herein have six CDR sequences provided in Table 1 above and have different amino acids in FR regions or Fc regions compared with the antibody created by any animal (e.g., human).

In certain embodiments, the antibodies or the antigen-binding fragments thereof provided herein have a specific binding affinity to SARS-CoV-2 which is sufficient to provide for preventive and/or therapeutic use.

The antibodies or antigen-binding fragments thereof provided herein can be a monoclonal antibody, a polyclonal antibody, a humanized antibody, a chimeric antibody, a recombinant antibody, a bispecific antibody, a multi-specific antibody, a labeled antibody, a bivalent antibody, an anti-idiotypic antibody, or a fusion protein. A recombinant antibody is an antibody prepared in vitro using recombinant methods rather than in animals.

In certain embodiments, the present disclosure provides a neutralizing antibody or antigen-binding fragment thereof, which competes for binding to SARS-CoV-2 with the antibody or antigen-binding fragment thereof provided herein. In certain embodiments, the present disclosure provides a neutralizing antibody or antigen-binding fragment thereof, which competes for binding to SARS-CoV-2 with an antibody: a) comprising a heavy chain variable region comprising the sequence of SEQ ID NO: 7, and a light chain variable region comprising the sequence of any of SEQ ID NO: 8; b) comprising a heavy chain variable region comprising the sequence of SEQ ID NO: 17, and a light chain variable region comprising the sequence of any of SEQ ID NO: 18; or c) comprising a heavy chain variable region comprising the sequence of SEQ ID NO: 27, and a light chain variable region comprising the sequence of any of SEQ ID NO: 28.

Antibody Variants

The antibodies and antigen-binding fragments thereof provided herein also encompass various variants of the antibody sequences provided herein.

In certain embodiments, the antibody variants comprise one or more mutations in one or more of the CDR sequences provided in Table 1 above, one or more of the non-CDR sequences of the heavy chain variable region or light chain variable region provided in Table 2 above, and/or the constant region (e.g. Fc region). Such variants retain binding specificity to SARS-CoV-2 of their parent antibodies, but have one or more desirable properties conferred by the mutation(s). For example, the antibody variants may have improved antigen-binding affinity, improved glycosylation pattern, reduced risk of glycosylation, reduced deamination, reduced or depleted effector function(s), improved FcRn receptor binding, increased pharmacokinetic half-life, pH sensitivity, and/or compatibility to conjugation.

The parent antibody sequence may be screened to identify suitable or preferred residues to be modified or substituted, using methods known in the art, for example, "alanine scanning mutagenesis" (see, for example, Cunningham and Wells (1989) Science, 244:1081-1085). Briefly, target residues (e.g. charged residues such as Arg, Asp, His, Lys, and Glu) can be identified and replaced by a neutral or negatively charged amino acid (e.g. alanine or polyalanine), and the modified antibodies are produced and screened for the interested property. If substitution at a particular amino acid location demonstrates an interested functional change, then the position can be identified as a potential residue for mutation. The potential residues may be further assessed by substituting with a different type of residue (e.g. cysteine residue, positively charged residue, etc.).

Affinity Variants

Affinity variants of antibodies may contain mutations in one or more CDR sequences provided in Table 1 above, the heavy or light chain variable region sequences provided in Table 2, or one or more FR sequences which can be readily identified by a person skilled in the art based on the CDR sequences provided in Table 1 and the heavy or light chain variable region sequences provided in Table 2, as it is well-known in the art that a CDR region is flanked by two FR regions in the variable region. The affinity variants retain specific binding affinity to SARS-CoV-2 of the parent antibody, or even have improved SARS-CoV-2 specific binding affinity over the parent antibody. In certain embodiments, at least one (or all) of the substitution(s) in the CDR sequences, FR sequences, or variable region sequences comprises a conservative substitution.

A person skilled in the art will understand that in the CDR sequences provided in Table 1 above, and variable region sequences provided in Table 2 above, one or more amino acid residues may be substituted yet the resulting antibody or antigen-binding fragment still retain the binding affinity or binding capacity to SARS-CoV-2, or even have an improved binding affinity or capacity. Various methods known in the art can be used to achieve this purpose. For example, a library of antibody variants (such as Fab or scFv variants) can be generated and expressed with phage display technology, and then screened for the binding affinity to SARS-CoV-2. For another example, computer software can be used to virtually simulate the binding of the antibodies to SARS-CoV-2, and identify the amino acid residues on the antibodies which form the binding interface. Such residues may be either avoided in the substitution so as to prevent reduction in binding affinity, or targeted for substitution to provide for a stronger binding.

In certain embodiments, the antibodies and antigen-binding fragments thereof provided herein comprises one or more amino acid residue substitutions in one or more of the CDR sequences, and/or one or more of the FR sequences. In certain embodiments, an affinity variant comprises no more than 20, 15, 10, 9, 8, 7, 6, 5, 4, 3, 2, or 1 substitutions in the CDR sequences and/or FR sequences in total.

In certain embodiments, the antibodies and antigen-binding fragments thereof provided herein comprise 1, 2, or 3 CDR sequences having at least 80% (e.g. at least 85%, 88%, 90%, 91%, 92%, 93%, 94%, 95%, 96%, 97%, 98%, 99%) sequence identity to that (or those) listed in Table 1 above yet retaining the specific binding to SARS-CoV-2 at a level similar to or even higher than its parent antibody.

In certain embodiments, the antibodies and antigen-binding fragments thereof provided herein comprise one or more variable region sequences having at least 80% (e.g. at least 85%, 88%, 90%, 91%, 92%, 93%, 94%, 95%, 96%, 97%, 98%, 99%) sequence identity to that (or those) listed in Table 2 above yet retaining the specific binding affinity to SARS-CoV-2 at a level similar to or even higher than its parent antibody. In some embodiments, the mutations occur in regions outside the CDRs (e.g. in the FRs).

Glycosylation Variants

The antibodies and antigen-binding fragments thereof provided herein also encompass glycosylation variants, which can be obtained to either increase or decrease the extent of glycosylation of the antibodies or antigen binding fragments thereof.

The antibodies or antigen binding fragments thereof may comprise one or more modifications that introduce or remove a glycosylation site. A glycosylation site is an amino acid residue with a side chain to which a carbohydrate moiety (e.g. an oligosaccharide structure) can be attached. Glycosylation of antibodies is typically either N-linked or O-linked. N-linked refers to the attachment of the carbohydrate moiety to the side chain of an asparagine residue, for example, an asparagine residue in a tripeptide sequence such as asparagine-X-serine and asparagine-X-threonine, where X is any amino acid except proline. O-linked glycosylation refers to the attachment of one of the sugars N-aceylgalactosamine, galactose, or xylose to a hydroxyamino acid, most commonly to serine or threonine. Removal of a native glycosylation site can be conveniently accomplished, for example, by altering the amino acid sequence such that one of the above-described tripeptide sequences (for N-linked glycosylation sites) or serine or threonine residues (for O-linked glycosylation sites) present in the sequence in the is substituted. A new glycosylation site can be created in a similar way by introducing such a tripeptide sequence or serine or threonine residue.

Cysteine-Engineered Variants

The antibodies and antigen-binding fragments thereof provided herein also encompass cysteine-engineered variants, which comprise one or more introduced free cysteine amino acid residues.

A free cysteine residue is one which is not part of a disulfide bridge. A cysteine-engineered variant is useful for conjugation with for example, a cytotoxic and/or imaging compound, a label, or a radioisoptype among others, at the site of the engineered cysteine, through for example a maleimide or haloacetyl. Methods for engineering antibodies or antigen-binding fragments thereof to introduce free cysteine residues are known in the art, see, for example, WO2006/034488.

Fc Variants

The antibodies and antigen-binding fragments thereof provided herein also encompass Fc variants, which comprise one or more amino acid residue mutations at the Fc region and/or hinge region, for example, to provide for altered effector functions such as ADCC and CDC. Methods of altering ADCC activity by antibody engineering have been described in the art, see for example, Shields R L. et al., *J Biol Chem.* 2001. 276(9): 6591-604; Idusogie E E. et al., *J Immunol.* 2000.164(8):4178-84; Steurer W. et al., *J Immunol.* 1995, 155(3): 1165-74; Idusogie E E. et al., *J Immunol.* 2001, 166(4): 2571-5; Lazar G A. et al., *PNAS,* 2006, 103(11): 4005-4010; Ryan M C. et al., *Mol. Cancer Ther.,* 2007, 6: 3009-3018; Richards J O. et al., *Mol Cancer Ther.*

2008, 7(8): 2517-27; Shields R. L. et al., *J. Biol. Chem,* 2002, 277: 26733-26740; Shinkawa T. et al., *J. Biol. Chem,* 2003, 278: 3466-3473.

CDC activity of the antibodies or antigen-binding fragments provided herein can also be altered, for example, by improving or diminishing C1q binding and/or CDC (see, for example, WO99/51642; Duncan & Winter Nature 322:738-40 (1988); U.S. Pat. Nos. 5,648,260; 5,624,821); and WO94/29351 concerning other examples of Fc region variants.

One or more amino acids selected from amino acid residues 329, 331 and 322 of the Fc region can be replaced with a different amino acid residue to alter C1q binding and/or reduced or abolished complement dependent cytotoxicity (CDC) (see, U.S. Pat. No. 6,194,551 by Idusogie et al.). One or more amino acid substitution(s) can also be introduced to alter the ability of the antibody to fix complement (see PCT Publication WO 94/29351 by Bodmer et al.).

Also encompassed herein are antibodies and antigen-binding fragments thereof provided herein having Fc variants with one or more amino acid residue mutations at the Fc region and/or hinge region, to provide for reduced or eliminated antibody dependent enhancement (ADE) of SARS-CoV-2 infection. Such Fc variants may have reduced binding to Fc receptors (FcR). Examples of such mutations include, without limitation, mutations of leucine residues at positions 4, 5, or both of CH2 domain (e.g. to alanine, as LALA variant), see, for example, WO2010043977A2, which is incorporated herein to its entirety.

Antigen-Binding Fragments

Provided herein are also neutralizing antigen-binding fragments against SARS-CoV-2. Various types of antigen-binding fragments are known in the art and can be developed based on the neutralizing antibodies against SARS-CoV-2 provided herein, including for example, the exemplary antibodies whose CDR are shown in Table 1 above, and variable sequences are shown in Table 2, and their different variants (such as affinity variants, glycosylation variants, Fc variants, cysteine-engineered variants and so on).

In certain embodiments, a neutralizing antigen-binding fragments against SARS-CoV-2 provided herein is a diabody, a Fab, a Fab', a F(ab')$_2$, a Fd, an Fv fragment, a disulfide stabilized Fv fragment (dsFv), a (dsFv)$_2$, a bispecific dsFv (dsFv-dsFv'), a disulfide stabilized diabody (ds diabody), a single-chain antibody molecule (scFv), an scFv dimer (bivalent diabody), a multispecific antibody, a camelized single domain antibody, a nanobody, a domain antibody, and a bivalent domain antibody.

Various techniques can be used for the production of such antigen-binding fragments. Illustrative methods include, enzymatic digestion of intact antibodies (see, e.g. Morimoto et al., *Journal of Biochemical and Biophysical Methods* 24:107-117 (1992); and Brennan et al., *Science,* 229:81 (1985)), recombinant expression by host cells such as *E. coli* (e.g. for Fab, Fv and ScFv antibody fragments), screening from a phage display library as discussed above (e.g. for ScFv), and chemical coupling of two Fab'-SH fragments to form F(ab')$_2$ fragments (Carter et al., *Bio/Technology* 10:163-167 (1992)). Other techniques for the production of antibody fragments will be apparent to a person skilled in the art.

In certain embodiments, the antigen-binding fragment is a scFv. Generation of scFv is described in, for example, WO 93/16185; U.S. Pat. Nos. 5,571,894; and 5,587,458. ScFv may be fused to an effector protein at either the amino or the carboxyl terminus to provide for a fusion protein (see, for example, Antibody Engineering, ed. Borrebaeck).

In certain embodiments, antibodies and antigen-binding fragments thereof provided herein are bivalent, tetravalent, hexavalent, or multivalent. Any molecule being more than bivalent is considered multivalent, encompassing for example, trivalent, tetravalent, hexavalent, and so on.

A bivalent molecule can be monospecific if the two binding sites are both specific for binding to the same antigen or the same epitope. This, in certain embodiments, provides for stronger binding to the antigen or the epitope than a monovalent counterpart. Similar, a multivalent molecule may also be monospecific. In certain embodiments, in a bivalent or multivalent antigen-binding moiety, the first valent of binding site and the second valent of binding site are structurally identical (i.e. having the same sequences), or structurally different (i.e. having different sequences albeit with the same specificity).

A bivalent can also be bispecific, if the two binding sites are specific for different antigens or epitopes. This also applies to a multivalent molecule. For example, a trivalent molecule can be bispecific when two binding sites are monospecific for a first antigen (or epitope) and the third binding site is specific for a second antigen (or epitope).

Conjugates

In some embodiments, the antibodies and antigen-binding fragments thereof provided herein further comprise one or more conjugate moieties. The conjugate moiety can be linked to the antibodies or antigen-binding fragments thereof. A conjugate moiety is a moiety that can be attached to the antibody or antigen-binding fragment thereof. It is contemplated that a variety of conjugate moieties may be linked to the antibodies or antigen-binding fragments thereof provided herein (see, for example, "Conjugate Vaccines", Contributions to Microbiology and Immunology, J. M. Cruse and R. E. Lewis, Jr. (eds.), Carger Press, New York, (1989)). These conjugate moieties may be linked to the antibodies or antigen-binding fragments thereof by covalent binding, affinity binding, intercalation, coordinate binding, complexation, association, blending, or addition, among other methods.

In certain embodiments, the antibodies or antigen-binding fragments thereof provided herein may be engineered to contain specific sites outside the epitope binding portion that may be utilized for binding to one or more conjugate moieties. For example, such a site may include one or more reactive amino acid residues, such as for example cysteine or histidine residues, to facilitate covalent linkage to a conjugate moiety.

In certain embodiments, the antibodies or antigen-binding fragments thereof may be linked to a conjugate moiety indirectly, or through another conjugate moiety. For example, the antibodies or antigen-binding fragments thereof provided herein may be conjugated to biotin, then indirectly conjugated to a second conjugate that is conjugated to avidin. In some embodiments, the conjugate moiety comprises a clearance-modifying agent (e.g. a polymer such as PEG which extends half-life), a detectable label (e.g. a luminescent label, a fluorescent label, an enzyme-substrate label), or other therapeutic molecules.

Examples of detectable label may include a fluorescent labels (e.g. fluorescein, rhodamine, dansyl, phycoerythrin, or Texas Red), enzyme-substrate labels (e.g. horseradish peroxidase, alkaline phosphatase, luceriferases, glucoamylase, lysozyme, saccharide oxidases or β-D-galactosidase), radioisotopes (e.g. $^{123}$I, $^{124}$I, $^{125}$I, $^{131}$I, $^{35}$S, $^{3}$H, $^{111}$In, $^{112}$In, $^{14}$C, $^{64}$Cu, $^{67}$Cu, $^{86}$Y, $^{88}$Y, $^{90}$Y, $^{177}$Lu, $^{211}$At, $^{186}$Re, $^{188}$Re, $^{153}$Sm, $^{212}$Bi, and $^{32}$P, other lanthanides), luminescent labels, chromophoric moieties, digoxigenin, biotin/avidin, DNA molecules or gold for detection.

In certain embodiments, the conjugate moiety can be a clearance-modifying agent which helps increase half-life of the antibody. Illustrative examples include water-soluble polymers, such as PEG, carboxymethylcellulose, dextran, polyvinyl alcohol, polyvinyl pyrrolidone, copolymers of ethylene glycol/propylene glycol, and the like. The polymer may be of any molecular weight, and may be branched or unbranched. The number of polymers attached to the antibody may vary, and if more than one polymer are attached, they can be the same or different molecules.

In certain embodiments, the conjugate moiety can be a purification moiety such as a magnetic bead.

In certain embodiments, the antibodies or antigen-binding fragments thereof provided herein is used as a base for a conjugate.

Pharmaceutical Composition

The present disclosure further provides pharmaceutical compositions comprising the neutralizing antibodies against SARS-CoV-2 or antigen-binding fragments thereof provided herein and one or more pharmaceutically acceptable carriers.

Pharmaceutical acceptable carriers for use in the pharmaceutical compositions disclosed herein may include, for example, pharmaceutically acceptable liquid, gel, or solid carriers, aqueous vehicles, nonaqueous vehicles, antimicrobial agents, isotonic agents, buffers, antioxidants, anesthetics, suspending/dispending agents, sequestering or chelating agents, diluents, adjuvants, excipients, or non-toxic auxiliary substances, other components known in the art, or various combinations thereof.

Suitable components may include, for example, antioxidants, fillers, binders, disintegrants, buffers, preservatives, lubricants, flavorings, thickeners, coloring agents, emulsifiers or stabilizers such as sugars and cyclodextrins. Suitable antioxidants may include, for example, methionine, ascorbic acid, EDTA, sodium thiosulfate, platinum, catalase, citric acid, cysteine, thioglycerol, thioglycolic acid, thiosorbitol, butylated hydroxanisol, butylated hydroxytoluene, and/or propyl gallate. As disclosed herein, inclusion of one or more antioxidants such as methionine in a composition comprising an antibody or antigen-binding fragment thereof and conjugates provided herein decreases oxidation of the antibody or antigen-binding fragment thereof. This reduction in oxidation prevents or reduces loss of binding affinity, thereby improving antibody stability and maximizing shelf-life. Therefore, in certain embodiments, pharmaceutical compositions are provided that comprise one or more antibodies or antigen-binding fragments thereof as disclosed herein and one or more antioxidants, such as methionine. Further provided are methods for preventing oxidation of, extending the shelf-life of, and/or improving the efficacy of an antibody or antigen-binding fragment provided herein by mixing the antibody or antigen-binding fragment with one or more antioxidants such as methionine.

To further illustrate, pharmaceutical acceptable carriers may include, for example, aqueous vehicles such as sodium chloride injection, Ringer's injection, isotonic dextrose injection, sterile water injection, or dextrose and lactated Ringer's injection, nonaqueous vehicles such as fixed oils of vegetable origin, cottonseed oil, corn oil, sesame oil, or peanut oil, antimicrobial agents at bacteriostatic or fungistatic concentrations, isotonic agents such as sodium chloride or dextrose, buffers such as phosphate or citrate buffers, antioxidants such as sodium bisulfate, local anesthetics such as procaine hydrochloride, suspending and dispersing agents such as sodium carboxymethylcelluose, hydroxypropyl methylcellulose, or polyvinylpyrrolidone, emulsifying agents such as Polysorbate 80 (TWEEN-80), sequestering or chelating agents such as EDTA (ethylenediaminetetraacetic acid) or EGTA (ethylene glycol tetraacetic acid), ethyl alcohol, polyethylene glycol, propylene glycol, sodium hydroxide, hydrochloric acid, citric acid, or lactic acid. Antimicrobial agents utilized as carriers may be added to pharmaceutical compositions in multiple-dose containers that include phenols or cresols, mercurials, benzyl alcohol, chlorobutanol, methyl and propyl p-hydroxybenzoic acid esters, thimerosal, benzalkonium chloride and benzethonium chloride. Suitable excipients may include, for example, water, saline, dextrose, glycerol, or ethanol. Suitable non-toxic auxiliary substances may include, for example, wetting or emulsifying agents, pH buffering agents, stabilizers, solubility enhancers, or agents such as sodium acetate, sorbitan monolaurate, triethanolamine oleate, or cyclodextrin.

The pharmaceutical compositions can be a liquid solution, suspension, emulsion, pill, capsule, tablet, sustained release formulation, or powder. Oral formulations can include standard carriers such as pharmaceutical grades of mannitol, lactose, starch, magnesium stearate, polyvinyl pyrollidone, sodium saccharine, cellulose, magnesium carbonate, etc.

In certain embodiments, the pharmaceutical compositions are formulated into an injectable composition. The injectable pharmaceutical compositions may be prepared in any conventional form, such as for example liquid solution, suspension, emulsion, or solid forms suitable for generating liquid solution, suspension, or emulsion. Preparations for injection may include sterile and/or non-pyretic solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use, and sterile and/or non-pyretic emulsions. The solutions may be either aqueous or nonaqueous.

In certain embodiments, unit-dose parenteral preparations are packaged in an ampoule, a vial or a syringe with a needle. All preparations for parenteral administration should be sterile and not pyretic, as is known and practiced in the art.

In certain embodiments, a sterile, lyophilized powder is prepared by dissolving an antibody or antigen-binding fragment as disclosed herein in a suitable solvent. The solvent may contain an excipient which improves the stability or other pharmacological components of the powder or reconstituted solution, prepared from the powder. Excipients that may be used include, but are not limited to, water, dextrose, sorbital, fructose, corn syrup, xylitol, glycerin, glucose, sucrose or other suitable agent. The solvent may contain a buffer, such as citrate, sodium or potassium phosphate or other such buffer known to a person skilled in the art at, in one embodiment, about neutral pH. Subsequent sterile filtration of the solution followed by lyophilization under standard conditions known to a person skilled in the art provides a desirable formulation. In one embodiment, the resulting solution will be apportioned into vials for lyophilization. Each vial can contain a single dosage or multiple dosages of the neutralizing antibody against SARS-CoV-2 or antigen-binding fragment thereof or composition thereof. Overfilling vials with a small amount above that needed for a dose or set of doses (e.g. about 10%) is acceptable so as to facilitate accurate sample withdrawal and accurate dosing. The lyophilized powder can be stored under appropriate conditions, such as at about 4° C. to room temperature.

Reconstitution of a lyophilized powder with water for injection provides a formulation for use in parenteral administration. In one embodiment, for reconstitution the sterile and/or non-pyretic water or other liquid suitable carrier is added to lyophilized powder. The precise amount depends upon the selected therapy being given, and can be empirically determined.

Kits

In certain embodiments, the present disclosure provides a kit comprising the antibody or an antigen-binding fragment thereof provided herein and/or the pharmaceutical composition provided herein. In certain embodiments, the present disclosure provides a kit comprising the antibody or an antigen-binding fragment thereof provided herein, and a second therapeutic agent. The second therapeutic agent can be a second SARS-CoV-2 neutralizing antibody, an antiviral agent such as RNA dependent RNA polymerase inhibitor, a nucleoside analog, antiviral cytokines (such as interferons), immunostimulatory agents, and other antiviral agents.

In certain embodiments, the second SARS-CoV-2 neutralizing antibody can be any antibody that has neutralizing activity on SARS-CoV-2, and optionally binds to an epitope that is different from those/that bound by the antibodies provided herein.

In certain embodiments, the second therapeutic agent is selected from the group consisting of Ivermectin, Colcrys (colchicine), Avigan (favipiravir) and other antiviral medications, Tamiflu (oseltamivir), Kaletra (lopinavir/ritonavir), Actemra (tocilizumab), Convalescent plasma, Azithromycin, Hydroxychloroquine and chloroquine, Dexamethasone, Remdesivir, Fluvoxamine, Bevacizumab, sarilumab, Tocilizumab, Corticosteroids, Nitazoxanide, Umifenovir, Famotidine, camostat, and Nafamostat.

Such kits can further include, if desired, one or more of various conventional pharmaceutical kit components, such as, for example, containers with one or more pharmaceutically acceptable carriers, additional containers etc., as will be readily apparent to a person skilled in the art. Instructions, either as inserts or a labels, indicating quantities of the components to be administered, guidelines for administration, and/or guidelines for mixing the components, can also be included in the kit.

Methods of Use

In one aspect, the present disclosure also provides methods of treating SARS-CoV-2 infection in a subject, comprising administering to the subject an effective amount of the antibody or antigen-binding fragment thereof provided herein, and/or the pharmaceutical composition provided herein.

In another aspect, the present disclosure also provides methods for preventing, inhibiting progression of, and/or delaying the onset of SARS-CoV-2 infection or an SARS-CoV-2-associated condition in a subject, comprising administering to the subject an effective amount of the antibody or antigen-binding fragment thereof provided herein, and/or the pharmaceutical composition provided herein.

In another aspect, the present disclosure also provides methods for preventing or reducing transmission of SARS-CoV-2 by a SARS-CoV-2 infected subject, comprising administering to the subject an effective amount of the antibody or antigen-binding fragment thereof provided herein, and/or the pharmaceutical composition provided herein.

In some embodiments, the present disclosure also provides methods for reducing viral load in a SARS-CoV-2 infected subject, comprising administering to the subject an effective amount of the antibody or antigen-binding fragment thereof provided herein, and/or the pharmaceutical composition provided herein.

The present disclosure also provides methods of neutralizing SARS-CoV-2 in a subject therewith.

In certain embodiments, the subject is human.

In certain embodiments, the subject is a human with or at risk for SARS-CoV-2 infection. SARS-CoV-2 infection can include, for example, infection of SARS-CoV-2 at respiratory tract, including nasal cavity infection, lower respiratory tract infection, or lung infection.

In certain embodiments, the subject is human exposed to or suspected of having exposure to SARS-CoV-2. The term "SARS-CoV-2 exposure" means being exposed to an environment where a SARS-CoV-2 carrier is present or has appeared. A "SARS-CoV-2 carrier" refers to any living or non-living subject with transmissible SARS-CoV-2 on or in it. "Transmissible SARS-CoV-2" refers to SARS-CoV-2 capable of spreading from one living or non-living subject to another living or non-living subject.

The term "effective amount" as used herein refers to a dosage of a medicament which can significantly eliminating, ameliorating or improving the symptoms associated with a disease or abnormal condition or which can produce the desired effect of preventing onset of symptoms associated with a disease or abnormal condition or even preventing the development of a disease or abnormal condition. The disease or abnormal condition can be associated with viral infection, such as SARS-CoV-2 infection. The effective amount of the antibodies or antigen binding fragment thereof of the present disclosure means the dosage thereof that can result in eliminating, ameliorating or improving symptoms associated with onset of SARS-CoV-2 infection symptoms, including but is not limited to, fever or chills, cough, shortness of breath or difficulty breathing, fatigue, muscle or body aches, headache, new loss of taste or smell, sore throat, congestion or runny nose, nausea or vomiting, and diarrhea; the effective amount of the antibodies or antigen binding fragment thereof of the present disclosure also means the dosage thereof that can effectively prevent SARS-CoV-2 infection or effectively prevent onset of SARS-CoV-2 infection symptoms.

The effective amount of an antibody or antigen-binding fragment provided herein will depend on various factors known in the art, such as body weight, age, past medical history, present medications, state of health of the subject and potential for cross-reaction, allergies, sensitivities and adverse side-effects, as well as the administration route and extent of disease development. Dosages may be proportionally reduced or increased by a person skilled in the art (e.g. physician or veterinarian) as indicated by these and other circumstances or requirements.

In certain embodiments, the administration dosage may change over the course of treatment. For example, in certain embodiments the initial administration dosage may be higher than subsequent administration dosages. In certain embodiments, the administration dosage may vary over the course of treatment depending on the reaction of the subject.

Dosage regimens may be adjusted to provide the optimum desired response (e.g. a therapeutic response). For example, a single dose may be administered, or several divided doses may be administered over time.

The antibodies or antigen-binding fragments thereof provided herein may be administered by any route known in the art, such as for example parenteral (e.g. subcutaneous, intraperitoneal, intravenous, including intravenous infusion, intramuscular, or intradermal injection) or non-parenteral (e.g. oral, intranasal, intraocular, sublingual, rectal, or topical) routes.

In some embodiments, the antibodies or antigen-binding fragments thereof provided herein may be administered alone or in combination with a therapeutically effective amount of a second therapeutic agent. For example, the antibodies or antigen-binding fragments thereof disclosed herein may be administered in combination with a second therapeutic agent, for example, a second SARS-CoV-2 neutralizing antibody, an antiviral agent such as RNA dependent RNA polymerase inhibitor, a nucleoside analog, antiviral cytokines (such as interferons), immunostimulatory agents, and other antiviral agents.

In certain of these embodiments, an antibody or antigen-binding fragment thereof provided herein that is administered in combination with one or more additional therapeutic agents may be administered simultaneously with the one or more additional therapeutic agents, and in certain of these embodiments the antibody or antigen-binding fragment thereof and the additional therapeutic agent(s) may be administered as part of the same pharmaceutical composition. However, an antibody or antigen-binding fragment thereof administered "in combination" with another therapeutic agent does not have to be administered simultaneously with or in the same composition as the agent. An antibody or antigen-binding fragment thereof administered prior to or after another agent is considered to be administered "in combination" with that agent as the phrase is used herein, even if the antibody or antigen-binding fragment and the second agent are administered via different routes. Where possible, additional therapeutic agents administered in combination with the antibodies or antigen-binding fragments thereof disclosed herein are administered according to the schedule listed in the product information sheet of the additional therapeutic agent, or according to the Physicians' Desk Reference 2003 (Physicians' Desk Reference, 57$^{th}$ Ed; Medical Economics Company; ISBN: 1563634457; 57$^{th}$ edition (November 2002)) or protocols well known in the art.

In another aspect, the present disclosure provides kits comprising the antibody or antigen-binding fragment thereof provided herein and/or the pharmaceutical composition provided herein, optionally conjugated with a detectable moiety, which is useful in detecting SARS-CoV-2 virus. The kits may further comprise instructions for use.

In another aspect, the present disclosure also provides use of the antibody or antigen-binding fragment thereof provided herein and/or the pharmaceutical composition provided herein in the manufacture of a medicament for treating or preventing SARS-CoV-2 infection in a subject; or for preventing, inhibiting progression of, and/or delaying the onset of SARS-CoV-2 infection or an SARS-CoV-2-associated condition in a subject; or for preventing or reducing transmission of SARS-CoV-2 by a SARS-CoV-2 infected subject; or for reducing viral load in a SARS-CoV-2 infected subject.

In another aspect, the present disclosure also provides use of the antibody or antigen-binding fragment thereof provided herein and/or the pharmaceutical composition provided herein in the manufacture of a diagnostic reagent for diagnosing SARS-CoV-2 infection.

The following examples are provided to better illustrate the claimed invention and are not to be interpreted as limiting the scope of the invention. All specific compositions, materials, and methods described below, in whole or in part, fall within the scope of the present invention. These specific compositions, materials, and methods are not intended to limit the invention, but merely to illustrate specific embodiments falling within the scope of the invention. A person skilled in the art may develop equivalent compositions, materials, and methods without the exercise of inventive capacity and without departing from the scope of the invention. It will be understood that many variations can be made in the procedures herein described while still remaining within the bounds of the present invention. It is the intention of the inventors that such variations are included within the scope of the invention.

EXAMPLES

Example 1: Materials and Methods

Human Samples

Peripheral blood mononuclear cells (PBMCs) from healthy control donors were collected from the Centre Hospitalier Universitaire of Université Laval (CHU-Université Laval), while PBMCs from COVID-19 survivors were obtained from SunnyBrook Hospital in Toronto. Ethical approval from ethic boards from both institutions were obtained prior to the sample collection and all participants signed an individual inform consent.

Fluorescent Cell Sorting

SARS-CoV-2 virus-like particles (VLP) (Medicago, Quebec, Canada) were biotinylated using EZ-Link™ Sulfo-NHS-Biotin according to the manufacturer's instruction (ThermoFisher scientific, Burlington, Canada).

PBMCs from COVID-19 survivors were thawed and rested for 30 minutes prior to staining using 1 µg of biotinylated SARS-CoV-2 VLP. Samples were then stained using a viability dye (Fixable Viability Dye eFluor, ThermoFisher), A488 coupled streptavidin (Biolegend, San Jose, Calif.), and a combination of lineage markers against CD14 (M5E2), CD3 (SP34-2), CD19 (HIB19), IgG (G18-145) and IgM (G20-127), all from BD Biosciences (San Jose, Calif.). After extensive washing of the samples, SARS-CoV-2 specific B cells were individually sorted using a FACSARIA Fusion (BD Biosciences). Sorted B cells were cultured for 2 weeks using feeder cells as previously described (Cox et al. mAbs 8:1, 129-140; 2016). Both supernatant and cells from SARS-CoV-2 specific B cell culture was collected for further analysis.

SARS-CoV-2 Specific Enzyme-Linked Immunosorbent Assay (ELISA)

Wells of a 96 well plate were coated overnight with 100 ng of SARS-CoV-2 VLP (Medicago). After extensive washing and blocking with PBS, 5% milk, wells were incubated with culture supernatant for 1 hour at 37° C. Following additional washes, wells were incubated with 15 ng of horseradish peroxidase (HRP) conjugated goat anti-human IgG (Mandel scientific, Guelph, Canada). After a final set of washes, wells were incubated with 2,2'-Azinobis [3-ethyl-benzothiazoline-6-sulfonic acid]-diammonium salt (ABTS) substrate (Mandel scientific) and the absorbance was read at 405 nm.

Recovery of Antibody Sequences

Antibody sequences were obtained as previously described (Cox et al. mAbs 8:1, 129-140; 2016). RNA was extracted from single cell-sorted B-cell cultures with Qiagen RNeasy Micro Kit (Qiagen) following manufacturer's instruction. The human antibody genes were amplified using Qiagen One-step RT-PCR kit (Qiagen, Cat. no: 210212). The RT-PCR primers were designed based on published sets (see Smith et al., Rapid generation of fully human monoclonal antibodies specific to a vaccinating antigen. Nat Proto 2009; 4:372-84). The RT-PCR products were used as templates in nested-PCR to amplify antibody variable regions with Invitrogen pfx50 DNA polymerase, the design for forward and reverse nested-PCR primers were based on sequences at the start of framework 1 region of human IgG heavy and light chain variable regions as described earlier (see Collarini et al., Potent high-affinity antibodies for treatment and prophylaxis of respiratory syncytial virus derived from B cells of infected patients. J Immunol 2009; 183:6338-45). The nested-PCR products were then used as templates in overlapping PCR to connect antibody light and heavy chain PCR products with a linker sequence and were cloned with infusion HD cloning kit (Clontech, Cat no: 639649) into a plasmid vector for sequencing.

SARS-CoV-2 Neutralization Assay

Test antibodies were recombinantly expressed in IgG1 form using HEK293 transient expression system (Sino Biological) for further assays. Vero-E6 cells were inoculated in 96-well cell culture plates (20,000 cells per well) with DMEM (Gibco) supplemented with 10% fetal bovine serum and grown overnight at 37° C. Antibodies with indicated concentration were mixed with 100 TCID50 SARS-CoV-2. The mixture was moved to the wells containing Vero-E6 cells and incubated at 37° C. for 1 hour. Following removing the supernatants, 200 µL cell culture medium were added and the plates were then incubated at 37° C. with 5% $CO_2$ for 3 days. Cells were stained with crystal violet and absorbance at 570 nm/630 nm were measured. Neutralization was defined as percentage reduction compared to positive controls. Neutralization titers of two replicates were calculated using a non-linear regression analysis in GraphPad Prism 7.

S Protein-Specific ELISA

Polystyrene microplates (Corning) were coated overnight with 0.1 or 1 µg/mL of SARS-CoV-2 S, S1 or RBD protein (Sino Biological). After washing with PBS containing 0.2% Tween 20, the plates were blocked using 2% BSA (Sigma Aldrich) in PBST for 1 hour at 37° C. Following washing with PBST, testing antibodies (1 ug/mL) were added to each well and incubated at 37° C. for 1 hour. After washing with PBST, HRP-conjugated goat anti-human IgG antibody was added at the dilution of 1:5000 and incubated at 37° C. for 1 hour. After washing, 3,3',5,5'-Tetramethylbenzidine (TMB) substrate solution was added to the microplate and incubated at room temperature for 6 min, followed by adding 2M $H_2SO_4$ to stop the reaction. The absorbance was detected at 450 nm.

Example 2: Characterization of the Antibodies

After screening all obtained antibodies by SARS-CoV-2 specific binding assay (data not shown), three best antibodies (i.e., 37G2, 31C2, and 15A7) were obtained. The SARS-CoV-2 specific binding activities of the three antibodies are shown in FIG. 1. The CDR regions of the antibodies were sequenced and listed in Table 1.

Figure 2:
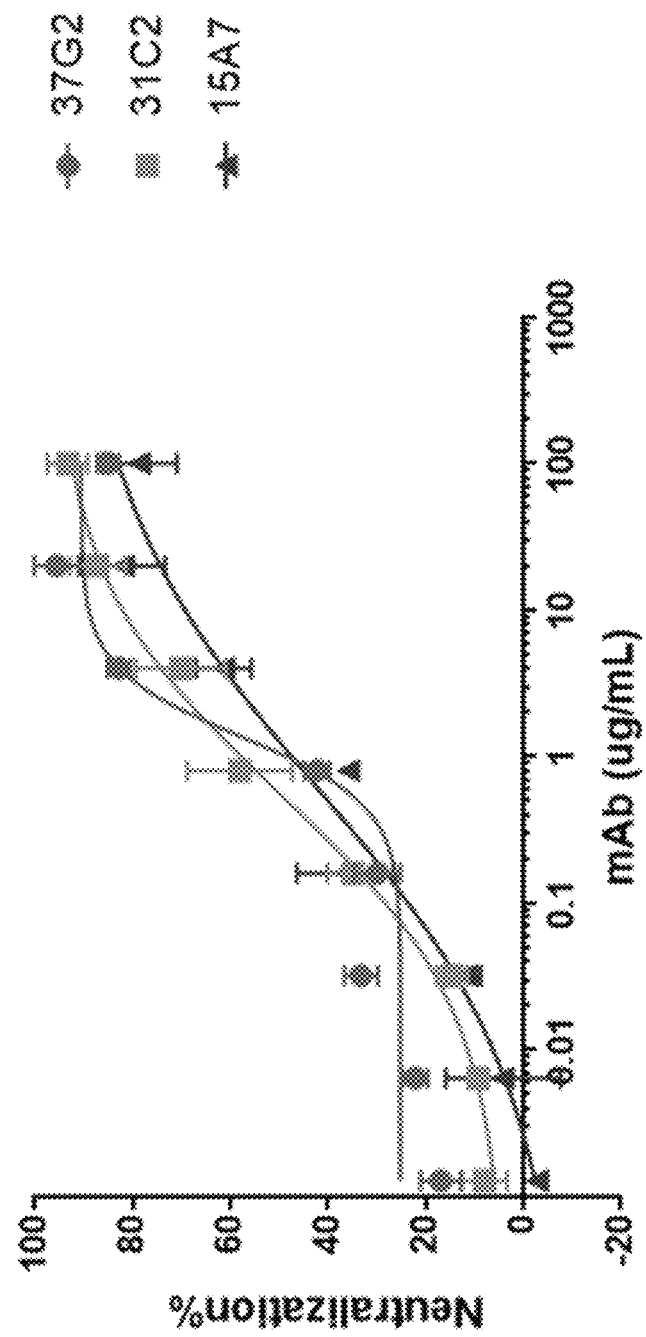
FIG. 2 shows neutralization of the antibodies provided in the disclosure to authentic SARS-CoV-2 in Vero-E6 cells.

These 3 antibodies were recombinantly expressed and subjected to an in vitro neutralizing assay using live virus in Vero-E6 cells. As shown in FIG. 2, all antibodies exhibit obvious neutralizing capacity against SARS-CoV-2 infection. The calculated $EC_{50}$ for 37G2, 31C2, and 15A7 are 1.37, 0.57, and 0.61 µg/mL, respectively.

Figure 3:
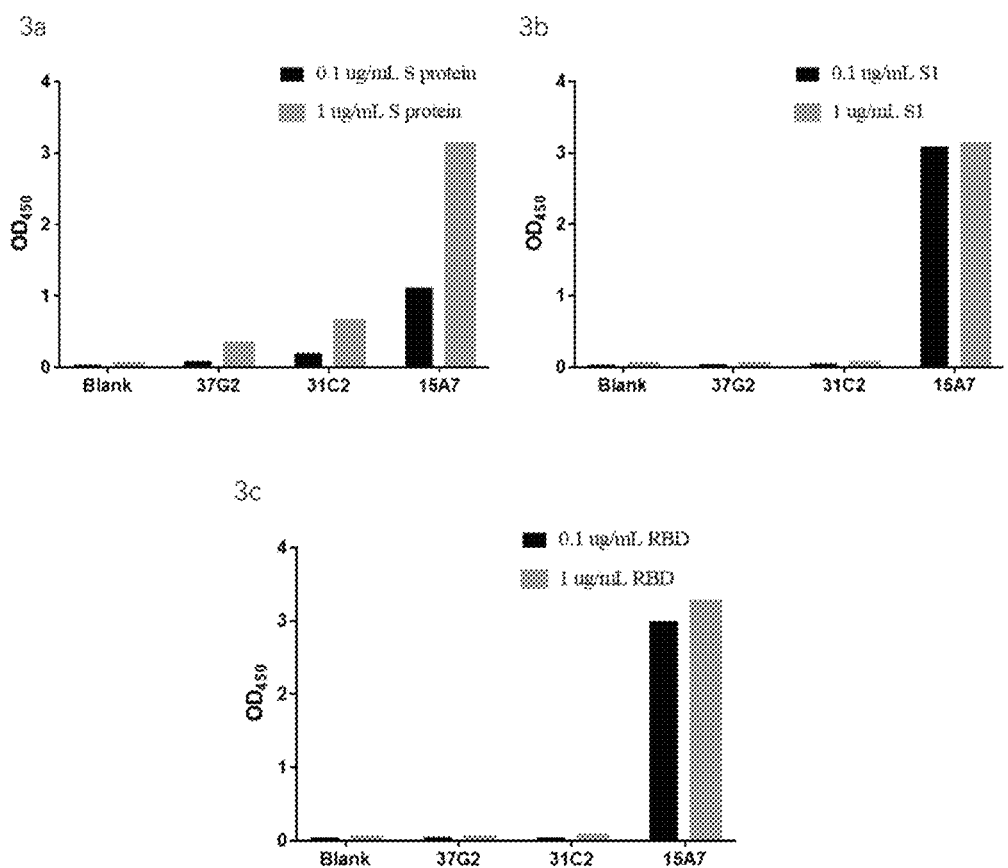
FIG. 3 shows binding profile of the antibodies provided in the disclosure with S protein (3a), S1 subunit (3b), and RBD (3c), as determined by ELISA.

We tested the binding properties of the antibodies with spike protein (S protein), S1 subunit, and RBD domain. As shown in FIG. 3, 15A7 binds to S protein, S1 subunit and RBD domain, suggesting that the antibody 15A7 blocks the interaction between SARS-CoV-2 and ACE2. The other two antibodies, 37G2 and 31C2, bind to S protein, but not to S1 subunit or RBD domain, suggesting that their binding site might be on S2 subunit of S protein.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. An expression vector, comprising an expression cassette comprising a nucleic acid sequence encoding a recombinant antibody, or an antigen-binding fragment thereof, capable of specifically binding to SARS-CoV-2, comprising: a heavy chain CDR1 (VH-CDR1) having an amino acid sequence of SEQ ID NO: 1, a VH-CDR2 having an amino acid sequence of SEQ ID NO: 2, a VH-CDR3 having an amino acid sequence of SEQ ID NO: 3, a light chain CDR1 (VL-CDR1) having an amino acid sequence of SEQ ID NO: 4, a VL-CDR2 having an amino acid sequence of SEQ ID NO: 5, and a VL-CDR3 having an amino acid sequence of SEQ ID NO: 6.

* * * * *